United States Patent
Zatezalo et al.

(10) Patent No.: US 6,643,537 B1
(45) Date of Patent: Nov. 4, 2003

(54) PROGRAMMABLE INJECTOR CONTROL

(75) Inventors: Douglas M. Zatezalo, Allison Park, PA (US); Jeffrey John Thompson, Allison Park, PA (US); Steven C. Rygg, Irwin, PA (US); Scott R. Griffith, Delmont, PA (US); John Gardner, Wexford, PA (US); Ronald J. Barbati, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 217 days.

(21) Appl. No.: 09/715,330

(22) Filed: Nov. 17, 2000

Related U.S. Application Data

(63) Continuation-in-part of application No. 09/365,278, filed on Jul. 30, 1999, now Pat. No. 6,339,718.

(51) Int. Cl.[7] ............................. A61B 6/00; A61M 5/00
(52) U.S. Cl. ..................... 600/432; 600/431; 600/458; 604/890.1; 604/892.1; 604/19
(58) Field of Search .......................... 604/890.1, 892.1, 604/19; 600/431, 432, 458

(56) References Cited

U.S. PATENT DOCUMENTS

| | | | |
|---|---|---|---|
| 3,888,239 A | * 6/1975 | Rubinstein | 128/2 |
| 4,006,736 A | 2/1977 | Kranys et al. | |
| 4,553,958 A | * 11/1985 | LeCocq | 604/67 |
| 4,677,980 A | 7/1987 | Reilly et al. | |
| 4,710,166 A | 12/1987 | Thompson et al. | |
| 5,304,126 A | * 4/1994 | Epstein et al. | 604/67 |
| 5,383,858 A | 1/1995 | Reilly et al. | |
| 5,472,403 A | * 12/1995 | Cornacchia et al. | 600/4 |
| 5,494,036 A | 2/1996 | Uber, III et al. | |
| 5,782,805 A | 7/1998 | Meinzer et al. | |
| 5,806,519 A | * 9/1998 | Evans, III et al. | 128/654 |

FOREIGN PATENT DOCUMENTS

| | | |
|---|---|---|
| EP | 0 192 786 | 9/1986 |
| EP | 0 302 752 | 2/1989 |

OTHER PUBLICATIONS

Injectron 82 MRT Operating Instructions, MR 1.4 Version, (Oct. 1997).
English Translation of Injectron 82 MRT Operating Instructions, MR 1.4 Version, (Oct. 1997).
Medrad Vistron CT Injection System Operation Manual; pp. 21–26 (2000); 95403–T–141, Rev. B.
International Search Report for Counterpart PCT Application No. PCT/US 00/120770.
MCT/MCT Plus Operation Manual, pp. 5–1 to 5–9 and 7–1 to 7–15, (1991); KMP 810P Rev. B.
Medrad Spectris MR Injector Operation Manual; pp. 2–1 to 2–18, 4–1 to 4–8 and 6–1 to 6–10 (1996); 92901–T–107, Rev E.
Medrad Envision CT Injector Operation Manual; pp. 2–1 to 2–36 and 4–1 to 4–13 (1995); 92401–T–123, Rev. E.

(List continued on next page.)

Primary Examiner—Marvin M. Lateef
Assistant Examiner—Jeoyuh Lin
(74) Attorney, Agent, or Firm—Gregory L. Bradley; Ian K. Sanways

(57) ABSTRACT

A fluid injection arrangement, particularly involving a systematic fluid injection programming capability, in the context of patient imaging systems, in which phases of contrast medium infection and flushing medium injection can be freely and selectably ordered so as to make available to the operator and patient a vast array of possible protocols than has hitherto been essentially unattainable. Also contemplated is the use of a "hold" phase, involving an indefinite pause between phases of a protocol, in connection with such imaging systems. Further contemplated is the use of a "pause" phase in which a pause of fixed duration is preprogrammed into the protocols of MRI Injector systems.

70 Claims, 21 Drawing Sheets

OTHER PUBLICATIONS

Optistar MR Injector System 510(k) Summary (Nov. 4, 1998).

Optistar MR Contrast Delivery System Brochure (2000).

Optistar MR Digital Injection System Operator's Manual, 801900-A (Nov. 1999).

MR Sonic Shot 50 Operator's Manual (with Accompanying English Translation of Chaper 11), Ver. 2.0.0 (Dec. 24, 1999).

Injektron 82 MRT User Instructions, Version MR2 (Mar. 10, 1999).

Medrad's *Amended Complaint,* Civil Action No. 01-1997-DEZ, Medrad, Inc. v. Tyco Healthcare Group LP, et al. (Jan. 15, 2002).

Tyco's *Answer and Counterclaim to Amended Complaint,* Civil Action No. 01-1997-DEZ, Medrad, Inc. v. Tyco Healthcare Group LP, et al. (Jan. 28, 2002).

Tyco's *Response to Medrad's First set of Interrogatories (Nos. 1-5),* Civil Action No. 01-1997-DEZ, Medrad, Inc. v. Tyco Healthcare Group LP, et al. (Mar. 18, 2002).

Tyco's *Supplemental Response to Medrad's First Set of Interrogatories (Nos. 1-5),* Civil Action No. 01-1997-DEZ, Medrad, Inc. v. Tyco Healthcare Group LP, et al. (Apr. 25, 2002).

Tyco's *Response to Medrad's Fourth Request for Production of Documents and Things,* Civil Action No. 01-1997-DEZ, Medrad, Inc. v. Tyco Healthcare Group LP, et al. (Jun. 24, 2002).

Medrad's *Second Amended Complaint,* Civil Action No. 01-1997-DEZ, Medrad, Inc. v. Tyco Healthcare Group LP, et al. (Mar. 26, 2002).

Tyco's *Answer and Counterclaim to Second Amended Complaint,* Civil Action No. 01-1997-DEZ, Medrad, Inc. v. Tyco Healthcare Group LP, et al. (Jul. 8, 2002).

Medrad's *Answer to Defendants' Counterclaim,* Civil Action No. 01-1997-DEZ, Medrad, Inc. v. Tyco Healthcare Group LP, et al. (Jul. 31, 2002).

Medrad's *Amended Answer to Defendants' Counterclaim,* Civil Action No. 01-1997-DEZ, Medrad, Inc. v. Tyco Healthcare Group LP, et al. (Aug. 9, 2002).

Tyco's *Preliminary Prior Art and Invalidity Chart as Applied to Claims of U.S. Patent No. 6,339,718 in Response to Interrogatory Nos. 2 and 3* (Spectris) (22 pages), Civil Action No. 01-1997-DEZ, Medrad, Inc. v. Tyco Healthcare Group LP, et al. (undated).

Tyco's *Prior Art and Invalidity Chart Claims of U.S. Patent No. 6,339,718 in Response to Interrogatory Nos. 2 and 3* (Nemoto Sonic Shot), Civil Action No. 01-1997 (13 pages) (undated).

Alleged Nemoto Operators' Manual (labeled MAL-P17-004295 to MAL-P17-004315).

Tyco's *Preliminary Noninfringement Chart Claims of U.S. Patent No. 6,339,718 in Response to Interrogatory No. 7,* Civil Action No. 01-1997-DEZ (10 pages) (Undated).

Nemoto's *Responses to Medrad's First Requests for Admissions (Nos. 1-25),* Civil Action No. 01-1997-DEZ (Dec. 2, 2002).

Tyco's *Responses to Medrad's First Set of Requests for Admissions Nos. 1-37,* Civil Action No. 01-1997-DEZ (Jan. 13, 2003)).

Tyco's *Second Supplemental Response to Medrad's First Set of Interrogatories (Nos. 1-5),* Civil Action No. 01-1997-DEZ (Jan. 15, 2003).

Photograph of Nemoto's Sonic Shot 50 MR Injector (labeled NEMOTO-012162) (undated).

Alleged Nemoto Instruction Manual for Sonic Shot 50 MR Injector (labeled NEMOTO-012137 to 012161) (undated).

Alleged Nemoto Instruction Manual for Sonic Shop 50 (labeled NEMOTO-011989 to NEMOTO-0120800 (Japanese and English).

*Update,* Clinical Imagiology, vol., 4, No. 6 (Jun. 1993) (labeled NEMOTO-012081 to NEMOTO-012089).

Tyco's *Response to Medrad's Fourth Set of Requests for Admissions (Nos. 54-79),* Civil Action No. 01-1997-DEZ (Mar. 31, 2003).

\* cited by examiner

PROGRAMMABLE INJECTOR CONTROL

CROSS-REFERENCE TO RELATED APPLICATIONS

This application is a continuation-in-part of application Ser. No. 09/365,278, now U.S. Pat. No. 6,339,718 filed on Jul. 30, 1999, the contents of which are hereby incorporated by reference.

BACKGROUND OF THE INVENTION

The present invention generally relates to powered injectors and syringes for use therewith, and more particularly, to methods and apparatus for automatically controlling the same.

A number of injector-actuated syringes and powered injectors for use in medical procedures such as angiography, computed tomography, ultrasound and NMR/MRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858.

U.S. Pat. No. 5,494,036 discloses a patient infusion system adapted for use in MRI. The infusion system is designed to be substantially non-reactive with the magnetic field generated by the magnetic resonance imaging system for producing diagnostic images.

Medrad has also developed a control arrangement ("SPECTRIS") for an MRI infusion system that uses two syringes, namely, one for the introduction of contrast medium into a patient and the other for a flushing medium. As is known conventionally, it is often desirable to flush from the tubing of an infusion system a residual quantity of contrast medium that remains there after a given infusion procedure, as contrast medium tends to be expensive and its efficient use, without waste, is often seen as a top priority. The "SPECTRIS" control arrangement will thus not only account for the residual contrast medium left in the tubing, and aim to use it in an infusion procedure, but will utilize a much cheaper flushing medium, such as a saline solution, in order to serve the purpose of pushing the residual contrast medium through the tubing and even through the patent's body (so as to "push" and deliver contrast medium to a region of interest in the body). Other advantageous purposes have also been recognized in connection with such flushing media, such as maintaining a flow through tie patient's veins for a predetermined period of time in order that the veins will be better prepared to subsequently receive a new infusion of contrast medium.

The "SPECTRIS" control arrangement is a pre-programmable arrangement for establishing a precise protocol for the infusion of contrast medium followed by flushing medium. At the time that the "SPECTRIS" system was established, needs in the industry were generally such that only some very simple protocols were desired. Thus, the "SPECTRIS" system addressed such needs by permitting protocols in which one or two "phases" of contrast medium took place followed by zero, one or two "phases" of flushing medium infusion. "Phase" refers to the application of a given quantity of a given medium at, for example, a fixed flowrate for a fixed period of time. Thus, up to two phases each of contrast medium and flushing medium, for example, were permitted by the "SPECTRIS" system, in order to provide a patient with different modes of infusion one after the other to serve particular purposes.

Of late, however, some disadvantages have been noted in connection with the "SPECTRIS" control system and other related systems. Not the least of these is the lack of flexibility in developing and administering infusion protocols to a patient, as the "SPECTRIS" system would allow no more than two distinct phases for each medium, and no single phase of flushing medium infusion could take place between two different phases of contrast medium infusion.

A further disadvantage has been recognized in that the aforementioned phases will typically be administered one after the other without the opportunity for an intermediate pause or hold between phases. This would appear to limit the convenience and utility of the system in question in many respects.

Nemoto and Co., Ltd., of Tokyo, Japan has also developed a control system for an MR injector. However, this appears to be even less flexible than the "SPECTRIS" system in that only protocols consisting of no more than one contrast medium infusion and no more than one flushing medium infusion appear to be permitted.

In the realm of CT (computed tomography) injection technology, Medrad has developed the "ENVISION" control system. As flushing media have generally not been hitherto employed in CT injector systems, the "ENVISION" system, much as any conventional CT injector control system, contemplates only the use of a single syringe for patient infusion, and solely for use with contrast medium. The "ENVISION" system permits protocols that employ up to eight different phases of contrast medium infusion, wherein each phase may employ a different infusion flowrate, infusion quantity and/or infusion duration. Pre-programmed pauses between infusion phases are also conceivable within such a context.

Evolving needs have thus been recognized in connection with providing an injection control system that is much more readily adaptable to a wider range of contexts.

SUMMARY OF THE INVENTION

Generally, at least one presently preferred embodiment of the present invention broadly contemplates a fluid injection arrangement, in the context of patient imaging systems, in which phases of contrast medium injection and flushing medium injection can be freely and selectably ordered so as to make available to the operator and patient a vast array of possible protocols that has hitherto been essentially unattainable.

The present invention also broadly contemplates the use of a "hold" phase, involving an indefinite pause between phases of a protocol, in connection with such imaging systems. One advantage of a "hold" phase is that it permits some time for the operator to render supplementary judgments, following the administration of the phase(s) before the "hold", that could be of value when administering the phase(s) that occur(s) after the "hold". For example, the "hold" phase could permit an operator to alter the parameters for the phases not yet undertaken.

In addition, the present invention broadly contemplates the use of "pattern recognition," through recognizing a graphical or iconic pattern of words, numbers, geometric shapes, and possibly other visual stimuli that in sum correspond to a given protocol, to permit an operator to quickly and efficiently recognize the makeup of a given protocol.

In one aspect, the present invention provides an apparatus and method for operating an injector providing stimuli corresponding to an injection protocol. The method includes perceiving the stimuli, recognizing a pattern provided by the stimuli, correlating the recognized pattern to the injection protocol, and interacting with the injector based on the recognized pattern.

The stimuli provided by the injector may, in a preferred embodiment of the present invention, comprise visual stimuli including, but not limited to, words, numbers, shapes and colors.

Also broadly contemplated herein is the use of a "pause" phase in which a pause of fixed duration is pre-programmed into the protocols of MRI injector systems.

In further summary, at least one presently preferred embodiment of the present invention broadly embraces fluid injection apparatus comprising: at least one drive mechanism; at least two fluid containers operably associated with the at least one drive mechanism, one fluid container containing a contrast medium and the other fluid container containing a flushing medium; and a control device operably associated with the at least one drive mechanism; wherein the control device is operable to: selectively program a plurality of phases of an injection procedure, at least one phase comprising one of: a contrast medium phase, a flushing medium phase, a pause phase and a hold phase; and selectively modify at least one phase of the injection procedure.

In addition, at least one presently preferred embodiment of the present invention broadly embraces a fluid injection apparatus comprising: at least one drive mechanism; at least two fluid containers operably associated with the at least one drive mechanism, one fluid container containing a contrast medium and the other fluid container containing a flushing medium; and a control device operably associated with the at least one drive mechanism; wherein at least one of the fluid containers includes an illumination element; and wherein the control device includes at least one element affiliated with the illumination element.

Additionally, at least one presently preferred embodiment of the present invention broadly embraces a fluid injection apparatus comprising: at least one drive mechanism; at least two fluid containers operably associated with the at least one drive mechanism, one fluid container containing a contrast medium and the other fluid container containing a flushing medium; and a control device operably associated with the at least one drive mechanism; wherein the control device is operable to: selectively program a plurality of phases of an injection procedure, at least one phase comprising one of: a contrast medium phase, a flushing medium phase, a pause phase and a hold phase; produce, during programming, a graphical display indicating at least the phases; and selectively recreate a facsimile of the graphical display at a subsequent time.

Furthermore, at least one presently preferred embodiment of the present invention broadly embraces a fluid injection apparatus comprising: at least one drive mechanism; at least two fluid containers operably associated with the at least one drive mechanism, one fluid container containing a contrast medium and the other fluid container containing a flushing medium; and a control device operably associated with the at least one drive mechanism; wherein the control device is operable to selectively program a plurality of phases of an injection procedure, at least one phase comprising one of: a contrast medium phase and a flushing medium phase; wherein the control device is further operable to selectively establish and control a KVO state independently from the programming of any of the phases.

Moreover, at least one presently preferred embodiment of the present invention broadly embraces a fluid injection apparatus comprising: at least one drive mechanism; at least two fluid containers operably associated with the at least one drive mechanism, one fluid container containing a contrast medium and the other fluid container containing a flushing medium; and a control device operably associated with the at least one drive mechanism; wherein the control device is operable to selectively program a plurality of phases of an injection procedure; at least one phase comprising one of: a contrast medium phase and a flushing medium phase; at least one phase comprising a hold phase.

Additionally, at least one presently preferred embodiment of the present invention broadly embraces a fluid injection apparatus comprising: at least one drive mechanism; at least two fluid containers operably associated with the at least one drive mechanism, one fluid container containing a contrast medium and the other fluid container containing a flushing medium; and a control device operably associated with the at least one drive mechanism; wherein the control device is operable to selectively program a plurality of phases of an injection procedure, at least one phase comprising one of: a contrast medium phase, a flushing medium phase, a pause phase and a hold phase; the control device further being operable to selectively store a protocol comprising a plurality of the phases and selectively recall the protocol at a subsequent time for use in an injection procedure.

Furthermore, at least one presently preferred embodiment of the present invention broadly embraces a fluid injection apparatus comprising: at least one drive mechanism; at least two fluid containers operably associated with the at least one drive mechanism, one fluid container containing a contrast medium and the other fluid container containing a flushing medium; and a control device operably associated with the at least one drive mechanism; wherein the control device is operable to selectively program a plurality of phases of an injection procedure; at least one phase comprising one of: a contrast medium phase and a flushing medium phase; at least one phase comprising a pause phase.

Numerous other objects and advantages of the present invention will be apparent from the following drawings and detailed description of the invention and its preferred embodiments.

BRIEF DESCRIPTION OF THE DRAWINGS

The present invention and its presently preferred embodiments will be better understood by way of reference to the detailed disclosure herebelow and to the accompanying drawings, wherein.

DETAILED DESCRIPTION OF THE INVENTION

Figure 1:
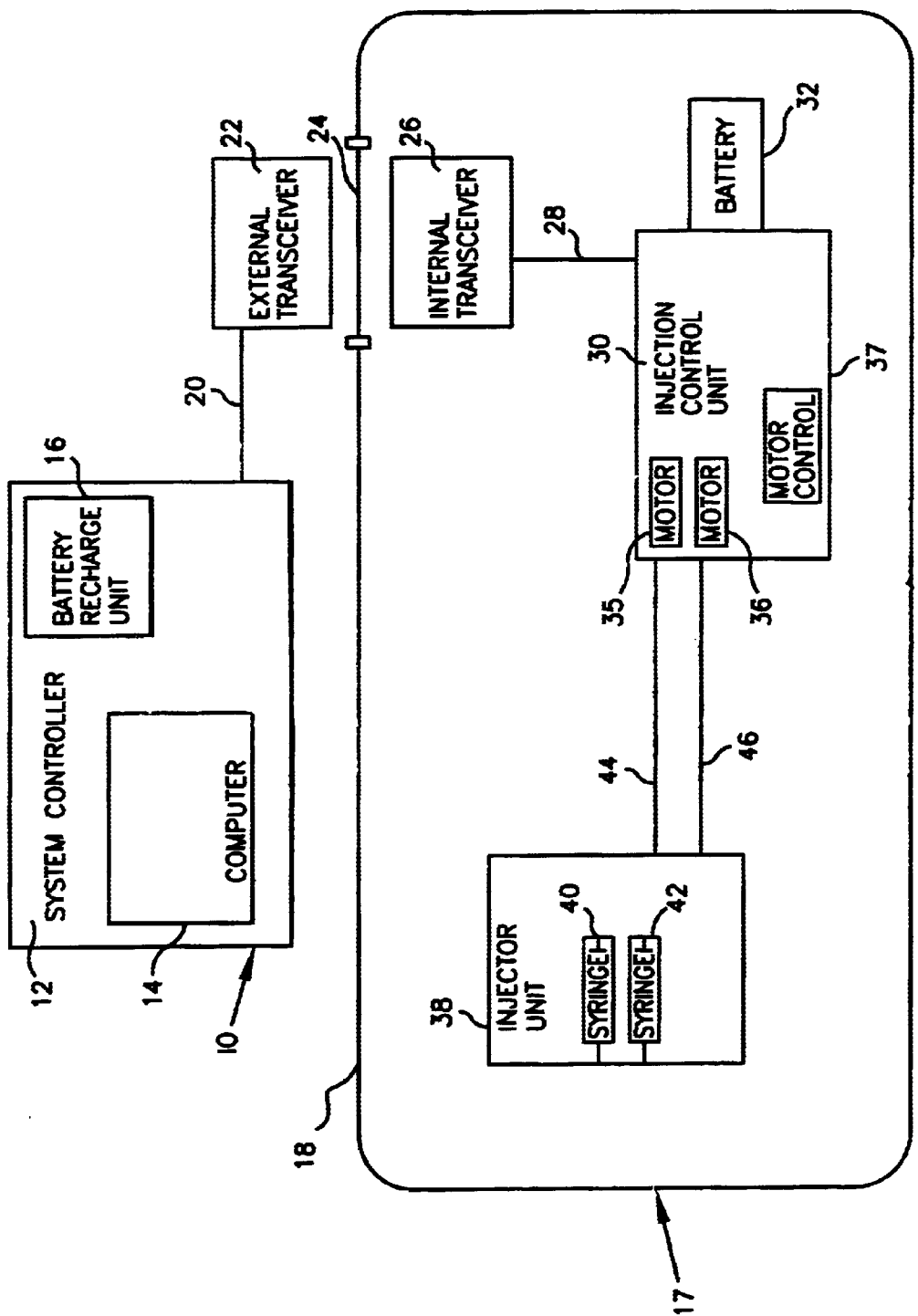
FIG. 1 is a schematic depiction of a conventional magnetic resonance imaging (MRI) injector system arrangement.
Figure 2:
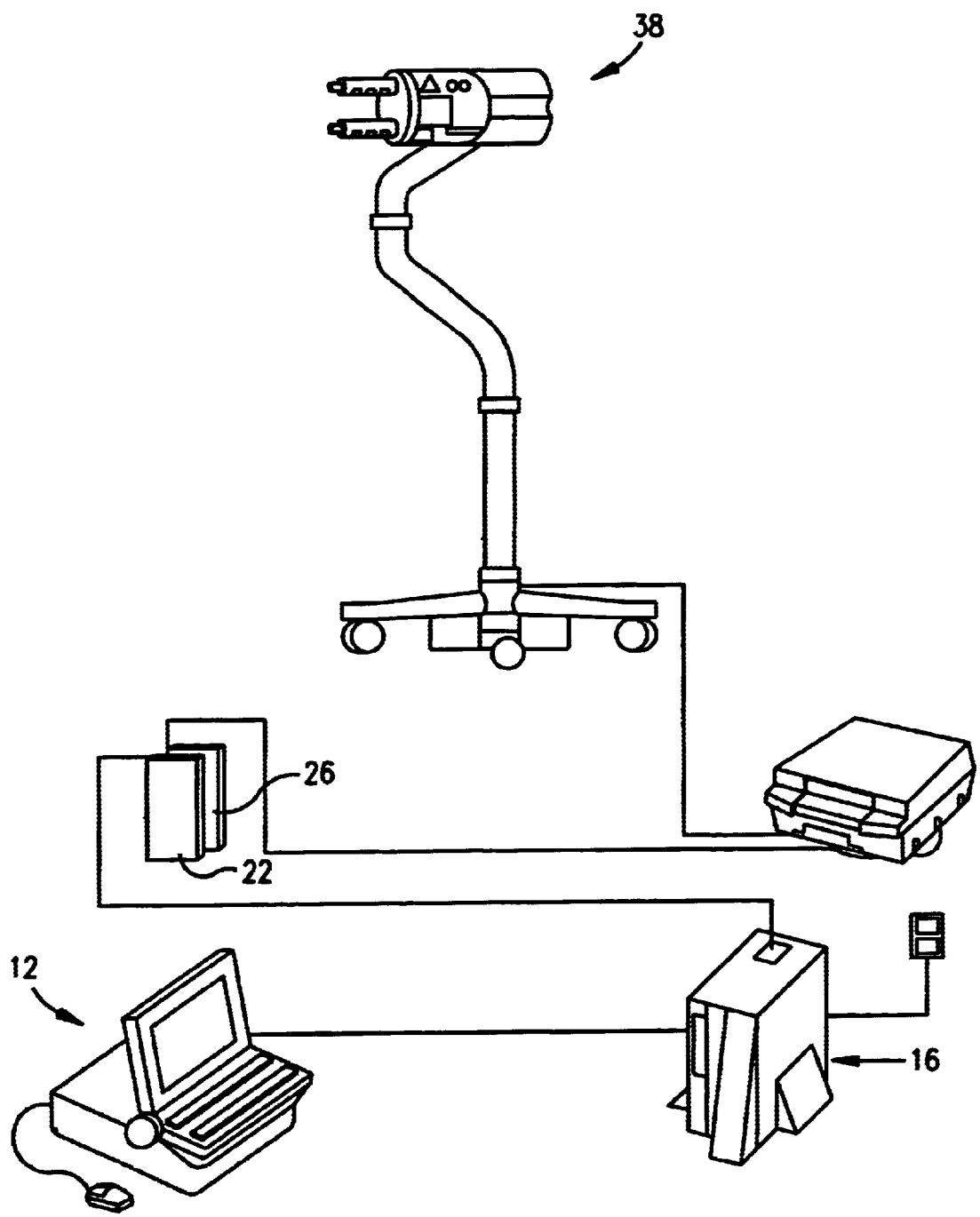
FIG. 2 is a pictographic depiction of a conventional MRI injector system arrangement.

FIGS. 1 and 2 generally illustrate a conventional MRI injector system arrangement, such as is disclosed in U.S. Pat. No. 5,494,036 to Uber et al, the contents of which are incorporated herein by reference. A magnetic resonance injector system is shown generally at 10. The MRI system includes a system controller 12, which incorporates a computer 14 and a battery charging unit 16. The system controller 12 is located externally of the imaging room, 7, the imaging room being shielded from electromagnetic interference by a shield 18.

Isolation can be achieved by completely enclosing the room with copper sheet material or some other suitable, conductive layer such as wire mesh. Communication line 20, connects the system controller 12 with an external infrared/optical communications transceiver 22. The shielded imaging room 17 also incorporates a patient viewing window 24 in the shield 18 which allows an operator to view the imaging room. The window 24 can be formed by sandwiching a wire mesh material (not shown) between sheets of glass or coating the window with al thin coating of conductive material such as gold (not shown) to maintain the continuity of the electromagnetic shield 18.

An infrared/optical communications transceiver 26 is positioned internally of the imaging room 17 at the viewing window 24 opposite the external communications transceiver 22 such that the internal and external communications transceivers communicate with each other through the viewing window with no breach of the electromagnetic shield. A communications link 28 located within the shielded area connects the internal infrared/optical transceiver with an injection control unit 30. The injection control unit 30 is powered advantageously by rechargeable battery 32. The injection control unit 30 also incorporates control circuitry that controls electric motors 35, 36 that are also located within the injection control unit. The injection control unit is contained within an electromagnetic shield 37 to prevent interference with the magnetic field used to generate the magnetic resonance image.

The injection head unit should preferably be located in close proximity to the patient in order to decrease the distance that the contrast media fluid must travel from the contrast media injectors. The injection head unit 38 includes contrast media injection syringe and piston units 40, 42. The syringes 40, 42 are in operation communicator with the electric motors in the injection control unit by flexible mechanical drive shafts 44, 46, respectively. The drive shafts are preferably made from a nonferrous metal such as hard brass.

The disclosure now turns to an embodiment of the present invention, as illustrated in FIGS. 3–6, that could conceivably be employed in connection with a MRI injector system such as that shown in FIGS. 1 and 2 or with any other of a wide range of MR, CT, angiographic or ultrasound injector systems. These possible uses of at least one embodiment of the present invention are elucidated in greater detail herebelow.

Shown schematically in FIGS. 3–6 are various incarnations of a touch screen arrangement 200 that could be employed in accordance with at least one presently preferred embodiment of the present invention. As a non-restrictive example, such a touch screen arrangement could be utilized in conjunction with a system controller 12 and computer 14 such as that described and illustrated hereinabove with respect to FIGS. 1 and 2. While a touch screen arrangement is contemplated in connection with FIGS. 3–6, it is to be understood that other types of data entry arrangements are conceivable that would achieve an equivalent purpose. Display fields 210, 220 could also be touch fields used for desired purpose. For example, soft or hard key entry could be used, as well as trackball arrangements, mouse arrangements, or a cursor control touch pad (remote from the screen).

Figure 3:
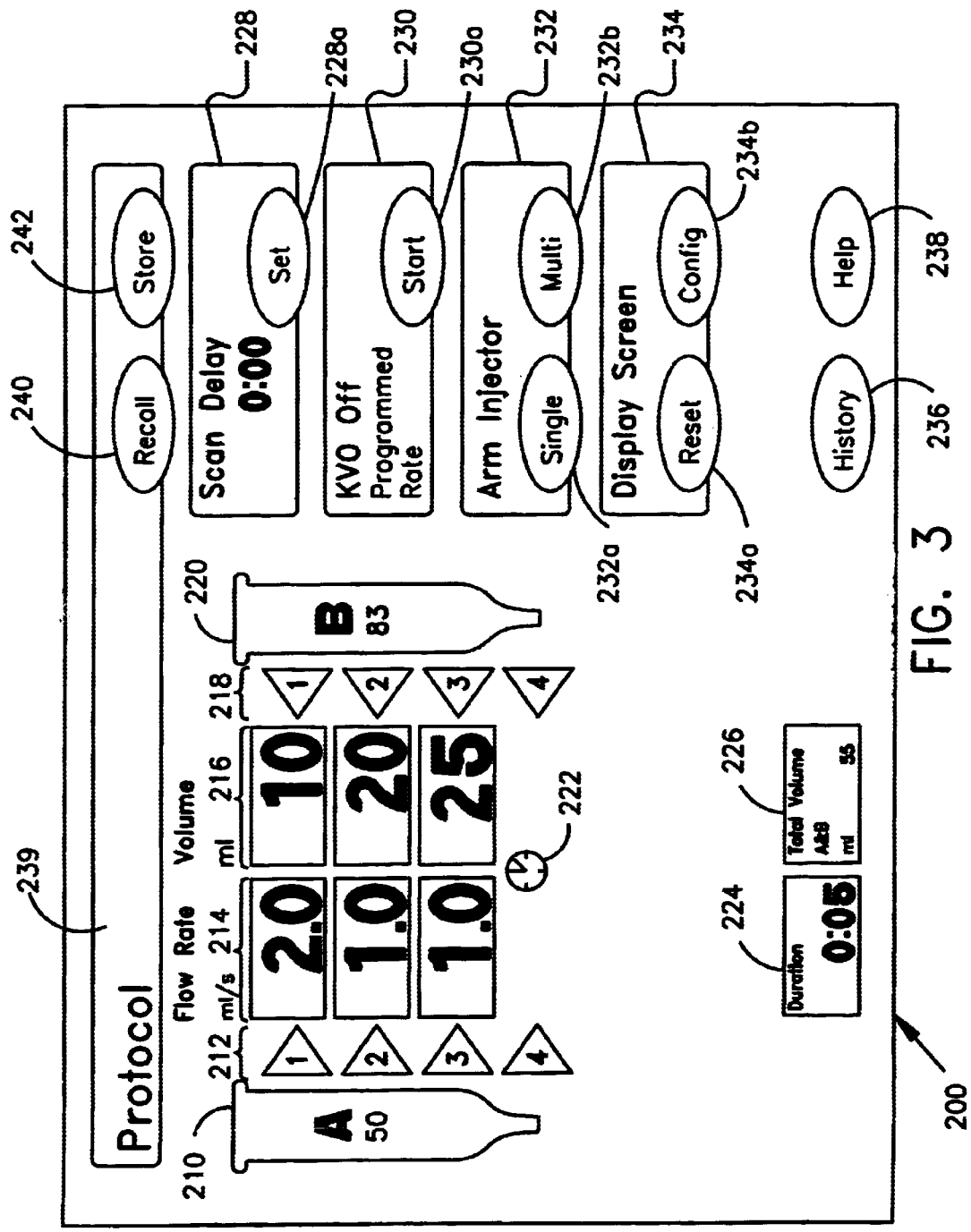
FIGS. 3–6 are various depictions of a control screen arrangement for use with different protocols.

As shown in FIG. 3, touch screen arrangement 200 may permit for the display of a display field 210 corresponding to the available quantity of contrast medium, a variable column 212 of touch fields for facilitating the entry of control parameters relating to contrast medium, a variable column 214 of touch fields relating to flowrate, a variable column 216 of touch fields relating to volume, a variable column 218 of touch fields for facilitating the entry of control parameters relating to flushing medium and a display field 220 corresponding to the available quantity of flushing medium. Display fields 210, 220 could also be touch fields used for a desired purpose.

The term "contrast medium", as employed herein, refers to essentially any suitable type of medium, as used in the medical arts, that is injected into a patient and, in the context of an imaging process (such as MR, angiography, ultrasound or CT), facilitates in highlighting selected areas of the patient's body while he/she is being scanned. In addition, the term "contrast medium", as employed herein, also refers to other diagnostic or therapeutic agents for injection into patients. The term "flushing medium", as employed herein, refers to essentially any suitable type of medium, such as a saline solution, that can be used to flush contrast medium from the tubing of an infusion system and that is well-suited for flowing through the patient's body so as to serve a useful supplementary purpose, such as keeping his/her veins open in preparation for another infusion of contrast medium.

As will be appreciated throughout this disclosure, the touch screen arrangement 200 is preferably configured for permitting the operator to freely and flexibly incorporate phases of contact medium infusion and phases of flushing medium infusion with respect to one another in a manner that has hitherto apparently not been contemplated nor realized. (A definition of "phases" may be found in the "Background" section of this disclosure). Further, the present invention also broadly contemplates, in accordance with at least one presently preferred embodiment, optional "hold" and "pause" phases as discussed herebelow.

Accordingly, FIG. 3 illustrates one conceivable protocol that may be entered in accordance with an embodiment of the present invention. As shown, displays 210 and 220 show that 50 ml of contrast medium are available, as are 83 ml of flushing medium. Also, the operator has selected the provision of two phases of contrast medium followed by one phase of flushing medium.

Preferably, the first phase of contrast medium infusion will have been set by activating the touch field 1 in column 212, followed by activating the corresponding entry fields in columns 214 and 216 and entering in them, respectively, the desired flowrate and desired volume to be administered to the patient. The entry of data can be accomplished by touching on a touch field (214 or 216), which could prompt the appearance of a key pad on the screen that would allow the entry of specific values in the fields 214, 216.

As shown, a second phase of contrast medium infusion has also been set in similar manner, but this time by activating touch field 2 in column 212, followed by activating the corresponding entry fields in columns 214 and 216 and again entering in them, respectively, the desired flowrate and volume.

For the third phase, as shown in FIG. 3, the operator has selected a flushing medium infusion phase, this time by activating touch field 3 in column 218 and then entering the desired flow rate and volume parameters in the corresponding fields in columns 214 and 216.

The result is a three-phase protocol that will result in the administration of: (1) a first phase of contrast medium infusion (10 ml) at 2.0 ml/s; (2) a second phase of contrast medium infusion (20 ml) at 1.0 ml/s; and (3) a phase of flushing medium infusion (25 ml) at 1.0 ml/s. Such a protocol might be desirable, for example, when it is desired that a patient first receive a first, quick infusion of contrast medium of smaller volume (i.e., a bolus of contrast medium) so as to accentuate (for imaging purposes) a small, particularized part of the body where such an infusion may be desirable, followed by a second, slower infusion of contrast medium of larger volume (e.g., a trickle or drip of contrast medium) that would be of use in a part of the body where a faster flowrate might not be needed. An example of such a part of the body may be (e.g., peripheral vascular regions of the legs). The flushing phase, then, could subsequently be utilized for purposes such as those described heretofore.

In a preferred embodiment of the present invention, touch screen arrangement 200 may be so configured as to display only those data entry fields in columns 214, 216 that have been specifically activated by the operator (via activation of corresponding touch fields in columns 212, 218), so that there will be no data fields visible in columns 214, 216 corresponding to phases that are not to be used for a given protocol. Thus, FIG. 3 shows that no data fields are visible in columns 214, 216 in correspondence with a fourth phase, since only three phases are being employed. Further, there will only preferably be one touch field in columns 212 and 218 visible beyond the number of phases that has already been chosen by the operator. Thus, as shown in FIG. 3, three phases have been entered and the touch fields 4 in columns 212 and 218 are visible in preparation for possible activation of a fourth phase by the operator. In the meantime, a suitable icon 222 (preferably having use in connection with a "hold" phase, as described later) may be provided in place of the absent data entry fields in columns 214 and 216. Accordingly, it will also preferably be the case that, prior to the activation of any phases at all, at an introductory stage of the process, no touch fields in columns 212–218 will be visible at all except for the touch fields 1 in the first row.

As shown, the incrementally emerging data fields in columns 214 and 216 may assume different shades, in correspondence with the type of phase being employed. Thus, in the embodiment illustrated in FIG. 3 (as well as FIGS. 4–6), the data entry fields assume a darker shade in correspondence with a contrast medium infusion phase, while they assume a lighter shade in correspondence with a flushing medium infusion phase. Further, the numbered touch fields in columns 212 and 218 may each preferably assume a corresponding shade in accordance with their being individually activated. Thus, fields 1 and 2 in column 212 are shaded in correspondence with their having been activated in the process of setting up two contrast medium infusion phases (following from their proximity to display field 210, which corresponds to contrast medium), while field 3 in column 218 is shaded in correspondence with its having been activated in the process of setting up a flushing medium infusion phase. In contrast, neither of the fields 4 in columns 212, 218 is shaded since neither has been activated to set up a phase of any sort.

The concept of incrementally emerging data fields in columns 214, 216, as discussed above, helps illustrate the flexibility and versatility afforded in accordance with at least one presently preferred embodiment of the present invention. Particularly, in the embodiment illustrated in FIG. 3, data fields emerge only to the extent that they are needed and can apply to either a contrast medium infusion phase or a flushing medium infusion phase at the behest of the operator. Such an arrangement would appear to stand in stark contrast to those conventional arrangements, such as the "SPECTRIS" arrangement described heretofore, in which the order of phases is comparatively fixed and inflexible. It should be appreciated that the presently contemplated arrangement also serves to reduce operator confusion and promotes the rapid visualization of important information.

Also illustrated in FIG. 3, inter alia, are a duration display field 224 and a total volume display field 226. These preferably will serve as, respectively, a clock of elapsed time that starts from zero and spans the duration of the totality of the phases that have been entered and an indicator of the total volume of fluid (destined for the patient) that has been expended over the totality of the phases. As shown in FIG. 3, duration display field 24 also preferably shows the projected total duration before injection starts, and volume display field 226 also preferably shows, at that time, the total projected volume to be expended.

Figure 4:
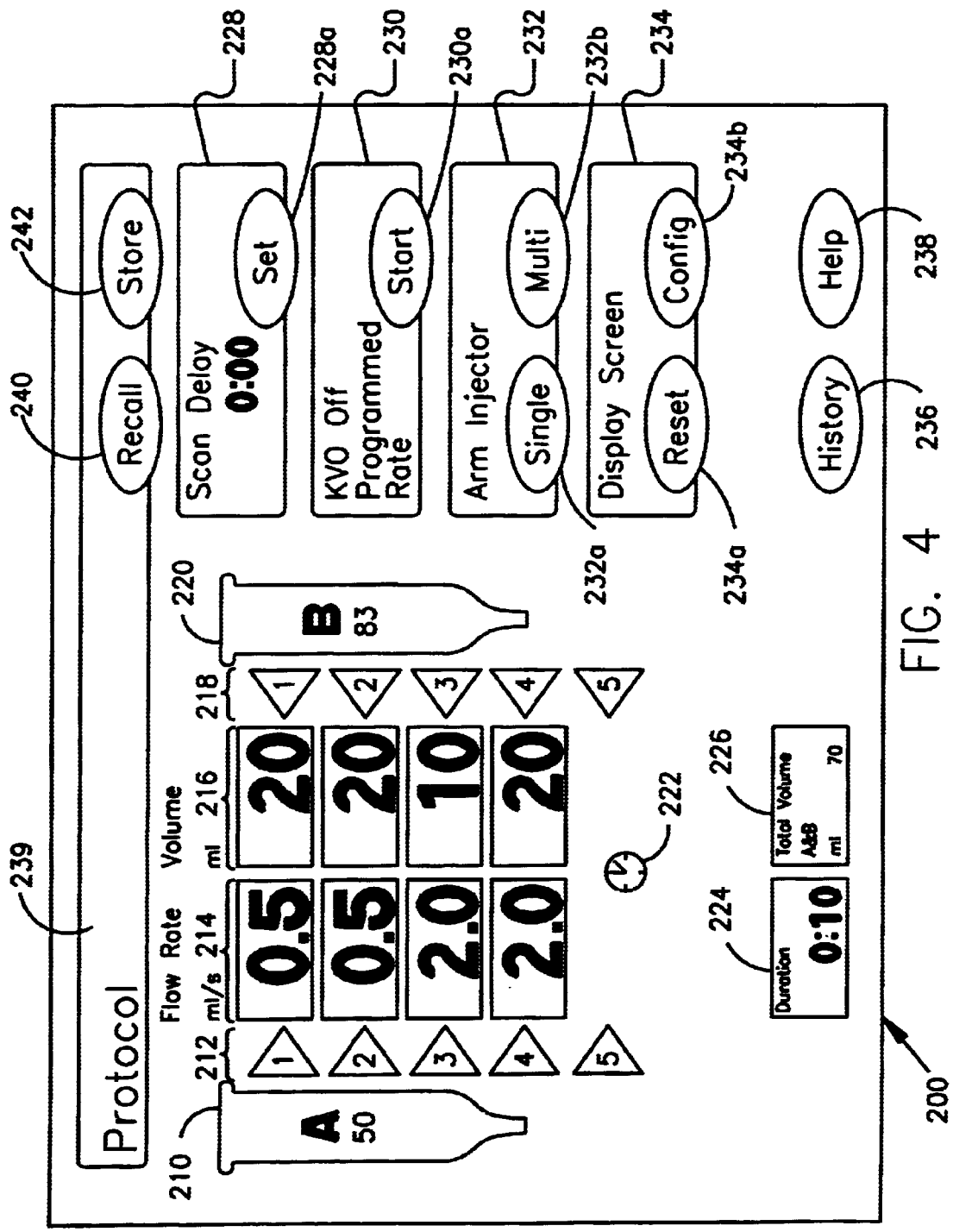
Figure 5:
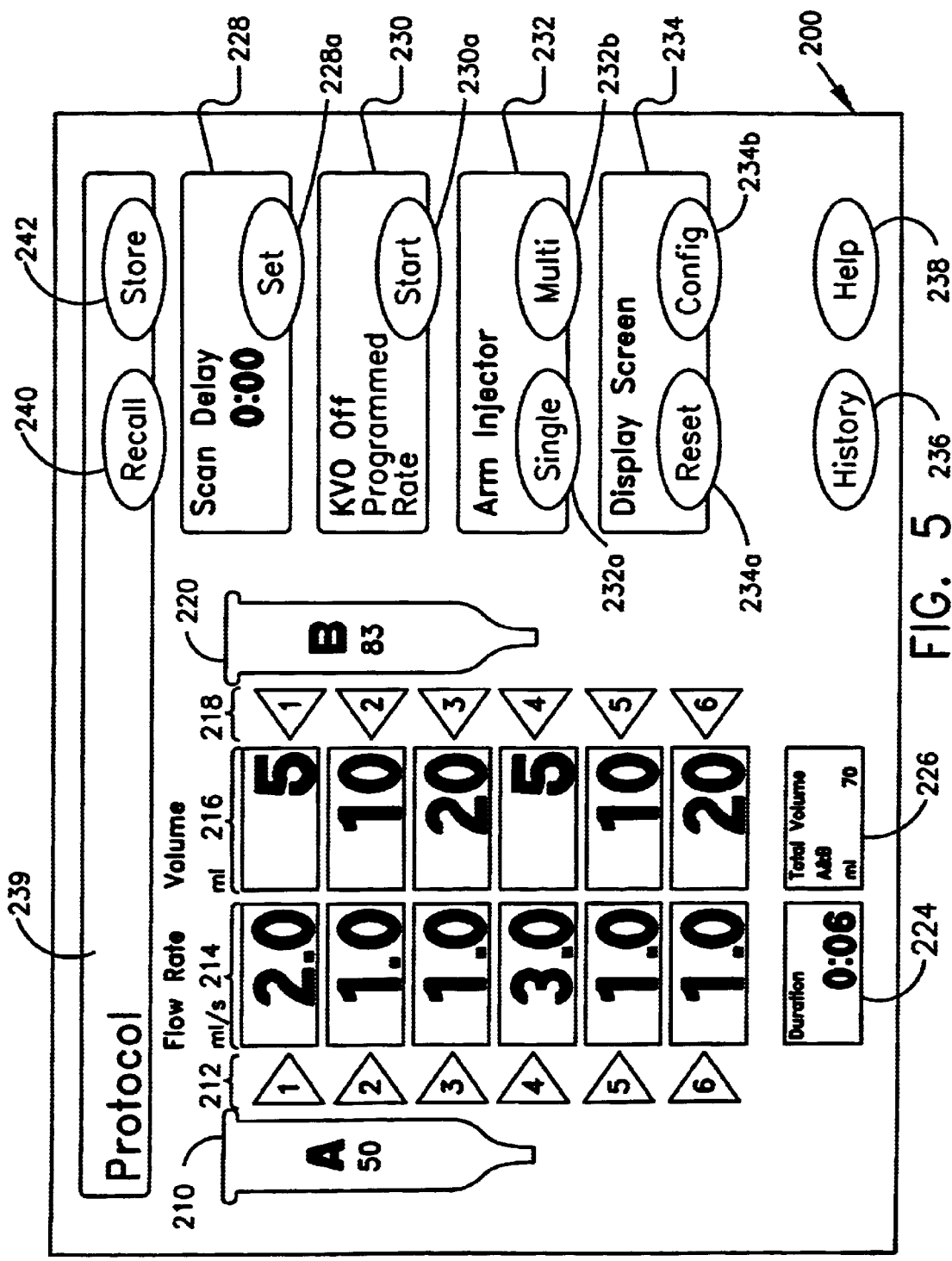
Figure 6:
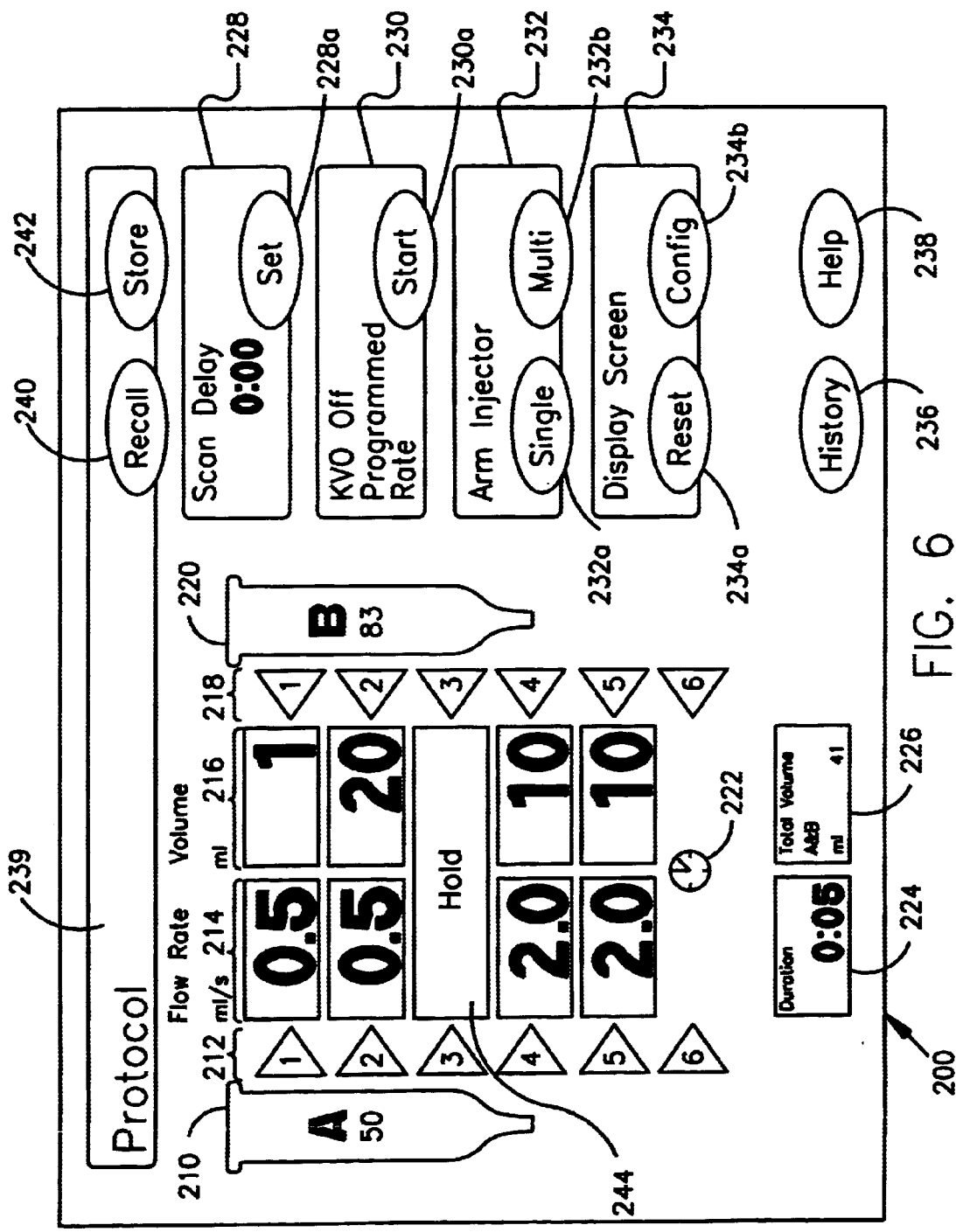

FIGS. 4–6 serve to further illustrate the versatility and flexibility afforded in accordance with at least one presently preferred embodiment of the present invention. Reference numerals in those figures relate to similar components referenced by similar numerals in FIG. 3.

In the protocol shown in FIG. 4, the operator has chosen a first phase of contrast medium infusion, followed by a first phase of flushing medium infusion, followed by a second phase of contrast medium infusion, finally followed by a second phase of flushing medium infusion.

FIG. 5 illustrates a different protocol, but this time involving six phases. Particularly, the six phases illustrated are two separate contrast medium phases, followed by a flushing medium phase, followed again by two distinct contrast medium phases, finally followed by a flushing medium phase.

Finally, FIG. 6 illustrates a protocol involving a distinct "hold" phase in accordance with an embodiment of the present invention. As shown here, the operator has selected a contrast medium phase followed by a flushing medium phase. However, the operator has also now selected a "hold" phase, indicated at 244, in which, for an indefinite period of time (possibly capped automatically for safety reasons), the regulated administration of fluids will cease, unless "KVO" (described below) is desired. The "hold" phase may be activated on touch screen arrangement 200 pressing on icon 222, which would then produce a "hold" display field 244 that spans both columns 214, 216. The "hold" phase is then followed by a second contrast medium phase and a second flushing medium phase.

The value of including a "hold" phase is that it permits some time for the operator to render supplementary judgements, following the administration of the phase(s) before the "hold", that could be of value when administering the phase(s) that occur(s) after the "hold". As an example, and as can be appreciated from the protocol shown in FIG. 6, the operator may wish to first infuse a short bolus of contrast medium not for imaging purposes but for the purpose of determining the length of time (by any suitable means) that the bolus requires in order to reach a given target area in the patient's body. Once a flushing phase is completed, the "hold" may then take effect. During the "hold", the imaging scanner (not shown here) could be programmed to delay its imaging action for a period of time that corresponds to the "delay" that the "short bolus" required in order to reach the target area of the body. In turn, the scan delay (i.e., the length of time that the scanner could "wait" before imaging the target area of the body) can be entered into a display field 228 by means of a touch field 228*a* suited for that purpose. Additionally, the operator may alter the parameters for the flowrate or volume for the phases not yet undertaken if observations undertaken during (or information derived from) the short bolus warrants changing such parameters.

When the time comes to administer the second contrast medium phase, the resulting bolus will be permitted to pass through the patient's system for a length of time corresponding to the "scan delay" before the scanner, conceivably prompted automatically via the scan delay clock in field 228 or perhaps manually by the operator (for example, upon hearing an audible signal), itself is activated as to image the target area of the patient.

It should be appreciated that among the advantages of the "hold" function are the elimination of operator interaction, as well as time savings, through eliminating the initial programming of a second injection phase. Additionally, an entire "short bolus" phase and subsequent standard injection phase may be stored and recalled as a "composite" injection type (see additional discussion further below), thus providing for rapid programming and reducing the chances of operator error. Furthermore, the hold function permits the optimization of the parameters of subsequent injections, thereby allowing for the improvement of overall image quality.

Other touch fields and display fields may be provided within touch screen arrangement 200. As shown in FIGS. 3–6, a KVO ("keep vein open") display field 230 may show the status of "KVO", that is, whether there is a circulation of flushing medium (either continuously or in small intermittent bursts) in the patient's system for the purpose of maintaining a flow of some type in his/her veins and perhaps to show a countdown of the time remaining in such a state. The duration of "KVO" could preferably be capped, in correspondence with the actual quantity of flushing medium available (minus the flushing medium required for any subsequent flushing medium phase), automatically by the control system. Thus, automatic shutoff could take place when the reservoir of available flushing medium has decreased to a point at which, with further depletion, there would not be a sufficient amount of flushing medium for a subsequent flushing medium phase or phases. It will be appreciated that "KVO" is not so much a flushing phase per se but instead is a "maintenance" phase in which the patient's veins are maintained in a relatively open state in preparation for the subsequent administration of contrast medium, or possibly even for other reasons. "KVO" could thus well take place during a "hold" phase so that, for example, the patient's veins could remain relatively open and free while the aforementioned intermediate calculations, etc., are taking place. Normally, the rate, volume and frequency of delivery in "KVO" are fixed ahead of time but it could also be variably programmed by the operator, by any suitable means.

The "arm injector" display field 232 and associated touch fields 232*a* and 232*b* serve the purpose of arming the injector and initiating the start of injection.

On the other hand, the "display screen" display field 234 and associated touch fields 234*a* and 234*b* serve the purpose of accessing any configuration (set-up) information such as language (e.g., English, German, French, Japanese, etc.) or KVO parameters or for reset (e.g. zeroing) of the screen.

The "history" display field 236 may serve the purpose of recalling past injection information that has been stored, while the "help" field 238 may serve the purpose of providing assistance to the operator in a manner similar to the "help" arrangements found on a typical computer or computer software system.

Finally, the "protocol" display field 239 and associated touch fields 240, 242 may serve the purposes of the identification, storage and recall of user-defined (saved) injection programs or (factory) pre-loaded programs.

Although the present invention, in accordance with at least one presently preferred embodiment, has been described hereinabove primarily in connection with an MR injector system, it is to be understood that other applications are possible without departing from the spirit and scope of the invention in general. For example, while it is known that CT, angiographic and ultrasound injectors to date have generally utilized only a single syringe, containing contrast medium, for administering solely contrast medium to a patient, the present invention broadly contemplates the use of two syringes in such environments—one for contrast medium and the other for flushing medium. Thus, it is contemplated that the present invention, in accordance with at least one presently preferred embodiment, could be utilized in such a context in that the operator could administer a protocol involving essentially any desired order of contrast medium and flushing medium phases.

A "pause" arrangement is also contemplated in accordance with at least one presently preferred embodiment of the present invention. A "pause" phase would essentially be similar to a "hold" phase in that it would represent a user-selected and programmed period of time in which no programmed injection of contrast medium or flushing medium is taking place. However, it would differ from a "hold" phase in the respect that it could essentially be a preprogrammed "hold" of limited duration that ends with an automatic transition to the next infusion phase (if any) in the protocol, whereas a "hold" phase would be of indefinite duration, with the protocol only to be reactivated by a manual prompt from the operator. Although "pause" phases have been known in conjunction with CT imaging arrangements, they are apparently not known in conjunction with MR imaging arrangements.

It should be appreciated that the inventive arrangements described hereinabove afford a degree of flexibility and versatility in programming an injection protocol than apparently has been hitherto realized. One distinct advantage inherent in such arrangements is their adaptability to foreseeable changes in the injection arts that may occur in the future, such as the development of new contrast media or increases in the efficiency of imaging scanners. For instance, it is conceivable that a different type of contrast medium might necessitate its injection into a patient via a much different protocol than might now normally be used with existing contrast media. Increases in imaging speed might also result in the need for vastly different types of protocols than are available on conventional equipment at present.

It will be appreciated that the flexibility and versatility achieved in accordance with at least one presently preferred embodiment of the present invention, with the use of an automatic arrangement, far outstrips any flexibility and versatility that might be gained through certain uses of existing injection arrangements. For example, although it is conceivable to employ two or more "SPECTRIS" systems for the purpose of executing a composite protocol, made up of separate protocols from the different systems, that might reflect a higher degree of versatility (e.g., by enabling the execution of a second contrast medium phase after a flushing medium phase), it will be appreciated that such an arrangement would be cumbersome, difficult to manage, and possibly inaccurate, in that one or more operators would need to ensure that one phase on one system starts immediately after another phase on another system. Manual injection is, of course, also possible, even to such an extent that different injections, representing distinctly different contrast medium and flushing medium phases, could be executed one after the other by one or more medical personnel. Again, though, such an arrangement would appear to prone to the potential of great inaccuracy, not only in terms of the timing of the successive injections but also in terms of the flowrates being used and the difficulty in keeping them constant over the duration of each phase (if indeed constant flowrates are desired).

Several other advantages would appear to be attainable in accordance with at least one presently preferred embodiment of the present invention. For example, an entire protocol, including short bolus, hold and remaining injection, can be stored and recalled for future use. The injector can reserve the flushing medium that is needed for an entire protocol and can alert the operator, before an injection commences, as to insufficient fluid volume. Moreover, in a multi-phased protocol that includes flushing and has an intermediate "hold" phase, the protocol can shut off flow in a "KVO" state automatically in order to preserve any necessary flushing medium for a subsequent pre-programmed flushing phase.

Although a maximum of six phases for one protocol has been described hereabove, it will be appreciated that the present invention broadly contemplates that no maximum on the number of phases in a protocol necessarily need be imposed.

Although all types of phases, especially contrast medium and flushing medium phases, have essentially been described hereinabove as being linear in nature (i.e., having a fixed flowrate over the duration of the phase), it should be understood that the present invention also broadly contemplates the programming and execution of phases that are not linear in nature. For example, it is conceivable that a contrast medium or flushing medium phase (and possibly even a "KVO" phase) could represent a non-linear function, in which the flowrate could possibly be variable over the duration of the phase and could be programmed in by means of an equation, lookup table or other suitable arrangement. In the case of "KVO", it is even conceivable that short "bursts" of flushing medium could be emitted at a variable rate instead of a fixed rate.

Although syringes have been specifically contemplated hereinabove for use in injection protocols, as a means for storing and administering contrasting medium or flushing medium, it is to be understood that other arrangements for this purpose are conceivable within the scope of the present invention, such as, for example, the use of peristaltic pumps.

As discussed herebelow, some additional refinements are broadly contemplated in accordance with at least one presently preferred embodiment of the present invention.

Figure 7:
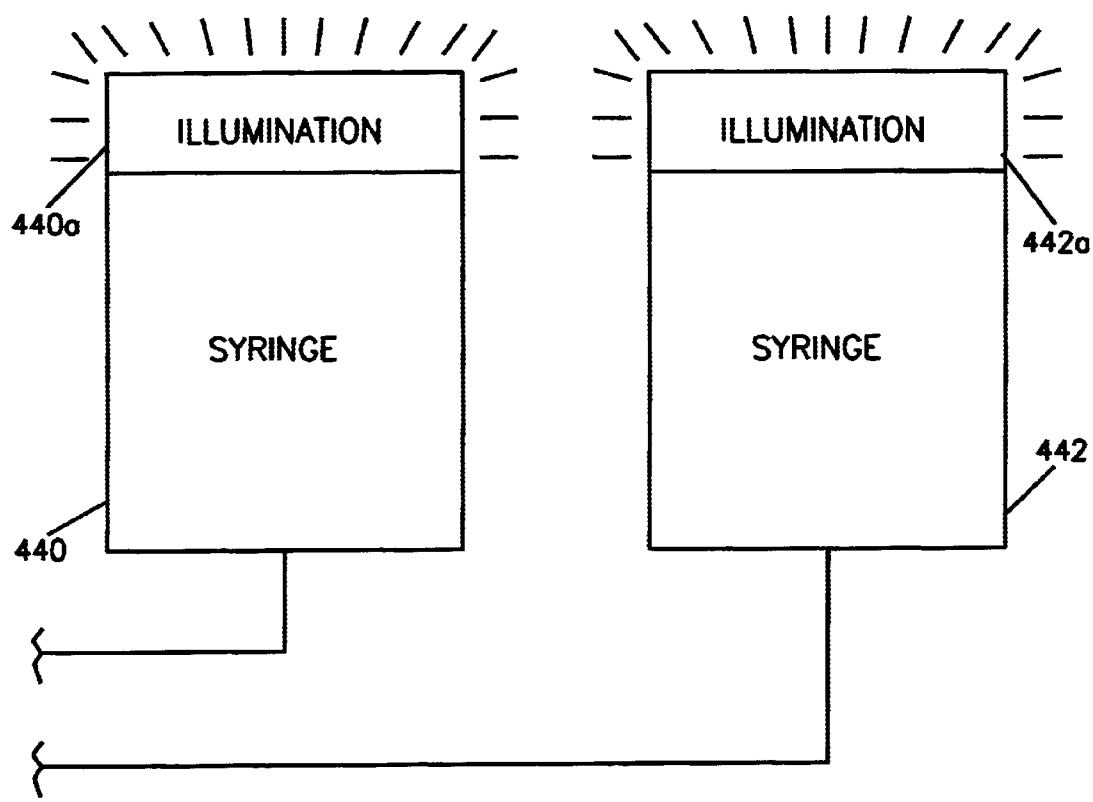
FIG. 7 is a schematic depiction of syringes with illumination elements.

FIG. 7 schematically illustrates a scheme of illumination in association with a pair of syringes 440, 442. Syringes 440, 442, may, for the purposes of illustration, substantially correspond to syringes or injectors for containing contrast medium and flushing medium, respectively, substantially as described heretofore.

Each syringe 440, 442 may have a corresponding illumination element 440a, 442a, respectively. The illumination elements 440a, 442a, may be configured as to provide an indication of a status or condition associated with each syringe 440, 442, so as to allow for the visual assessment of such a status or condition from a distance. For instance, the illumination elements 440a, 442a, could be configured for issuing light of different colors (e.g. green light for contrast medium and blue light for flushing medium) to permit one to easily distinguish between the two syringes. Illumination elements 440a/442a, possibly in combination with corresponding symbols or icons on a computer screen, could assume different states depending on system status (e.g. "flashing" for "armed" status, "steady" [illumination] for "injection" status and "off" for "disarmed" status.)

FIGS. 8–20 relate to modified touch screens in accordance with at least one presently preferred embodiment of the present invention.

While several components associated with the touch screens illustrated in FIGS. 8–20 are similar to those illustrated in FIGS. 3–6, other new or modified components are also contemplated, as discussed herebelow.

Figure 8:
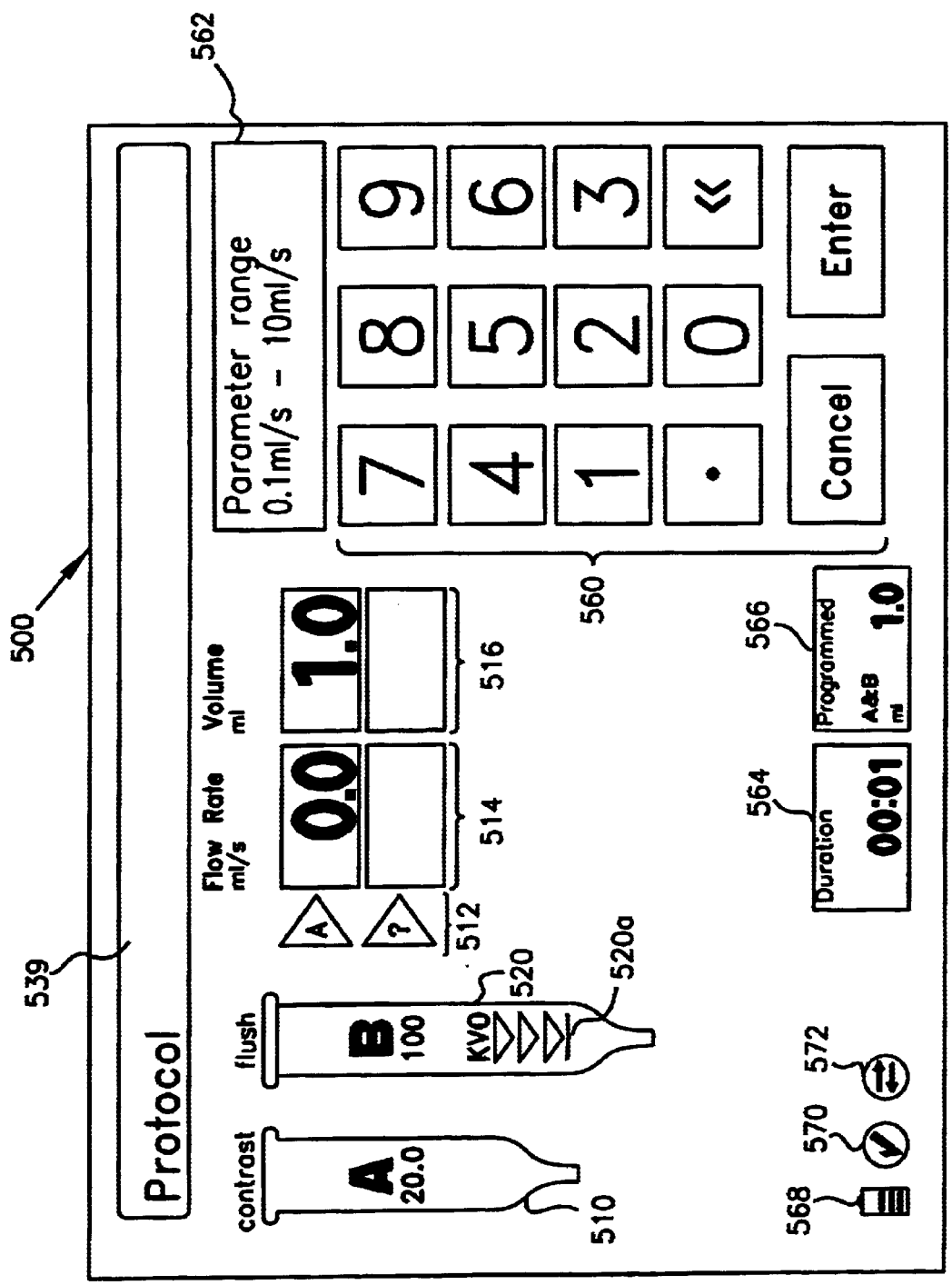
FIGS. 8 and 9 are depictions of a control screen arrangement for use with another protocol.

As shown in FIG. 8, touch screen arrangement 500 may permit for the display of a display field 510 corresponding to the available quantity of contrast medium and a variable column 512 of touch fields for indicating the status of ore or more phases that may be employed. Included also are a variable column 514 of touch fields relating to flowrate, a variable column 516 of touch fields relating to volume, and a display field 520 corresponding to the available quantity of flushing medium. Display fields 510, 520 could also be touch fields. Iconography 520a, adapted to appear and disappear within touch field 520, could indicate whether a "KVO" state is in effect.

Essentially, FIG. 8 illustrates an "initiation screen" prior to entering a protocol. As shown, displays 510 and 520 show that 20 ml of contrast medium are available, as are 100 ml of flushing medium, while, in the protocol columns 514, 516, no flow rate has yet been established and a token volume of 1.0 ml of contrast medium is shown.

Preferably, a first phase of contrast medium infusion can be set by activating the uppermost touch field in column 512, and thence the corresponding entry fields in columns 514 and 516, followed by entering in the latter two entry fields, respectively, the desired flowrate and desired volume to be administered to the patient. The entry of data can be accomplished when, upon touching on a touch field (514 or 516), a key pad 560 appears on the screen that allows the entry of specific values in the fields 514, 516.

Figure 9:
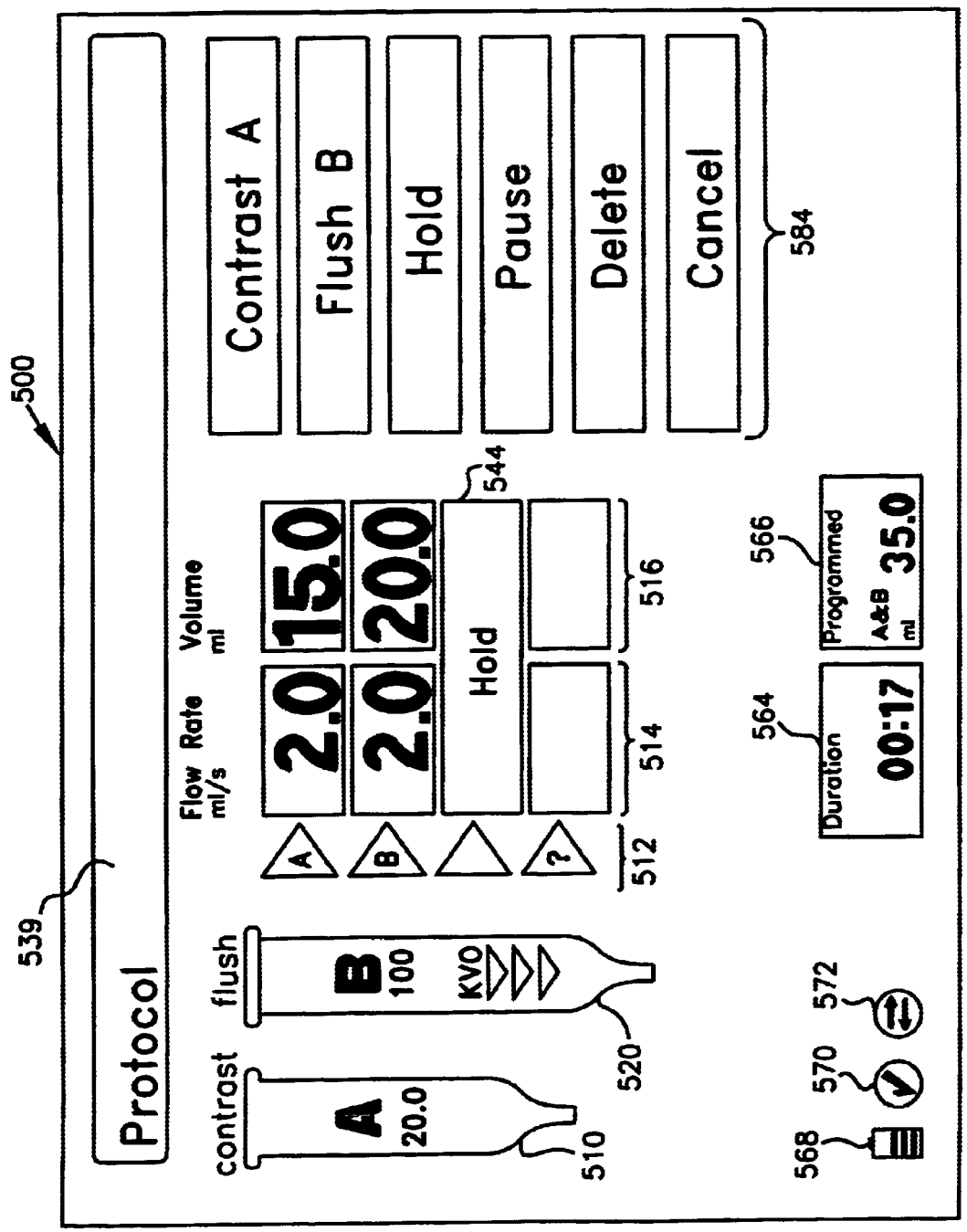

In order to establish the first phase as contrast, the touching of the uppermost field in column 512 may preferably prompt the appearance of a pop up selection table 584 (see FIG. 9). There, one may select the type of phase desired, particularly, contrast, flush, hold or pause.

Field 562 may be configured to convey to the operator a range of parameters that may be used in a given field in column 514 or 516. For this purpose, it is conceivable to draw attention to the field in question by highlighting it with a distinct color. As shown in FIG. 8, for example, the topmost field in column 514 is highlighted in black.

FIG. 9 illustrates the entry of a protocol involving a contrast phase, a flushing phase and, in addition, a hold phase. Thus, the three phases that result are: (1) a phase of contrast medium infusion (15 ml) at 2.0 ml/s; (2) a phase of flushing medium infusion (20 ml) at 2.0 ml/s; and (3) a hold phase similar to that described heretofore.

As introduced above, FIG. 9 also illustrates the optional pop up selection table 584 that permits a choice, for a given phase, of any of: a contrast phase, a flush phase, a hold or a pause. (The concept of "pause" has also been discussed heretofore.) "Delete" and "cancel" touch fields permit, respectively, erasing the previous entry or removing table 584 altogether.

Also illustrated in FIGS. 8 and 9, inter alia, are a duration display field 564 and a total volume display field 566. These preferably will serve as, respectively, a clock of elapsed time that starts from zero and spans the duration of the totality of the phases that have been entered and an indicator of the total volume of fluid (destined for the patient) that has been expended over the totality of the phases. As shown in FIGS. 8 and 9, duration display field 564 also preferably shows the projected total duration before injection starts, and volume display field 566 also preferably shows, at that time, the total projected volume to be expended. Display field 566 may also preferably be configured to illustrate the total volume (of both contrast and flushing medium) already delivered.

FIGS. 8 and 9 illustrate that three icons (or "status buttons") 568, 570, 572 may be employed. Icon 568, in the shape of a battery, indicates battery level. The number of horizontal bars within icon 568 indicates the useful life of the battery that remains. Icon 570, embodied as a check mark, can serve the function of an indicator for the status of the "check for air" function (e.g., the operator may first check to see if any air exists in the syringes and then activate the "check for air" status button 570.) Icon 572, on the other hand, embodied as opposing arrows, can confirm whether a digital interface with a scanner is established (e.g., for information exchange between the injector and scanner or for the transfer of programming and control functionality between the injector and scanner).

Figure 10:
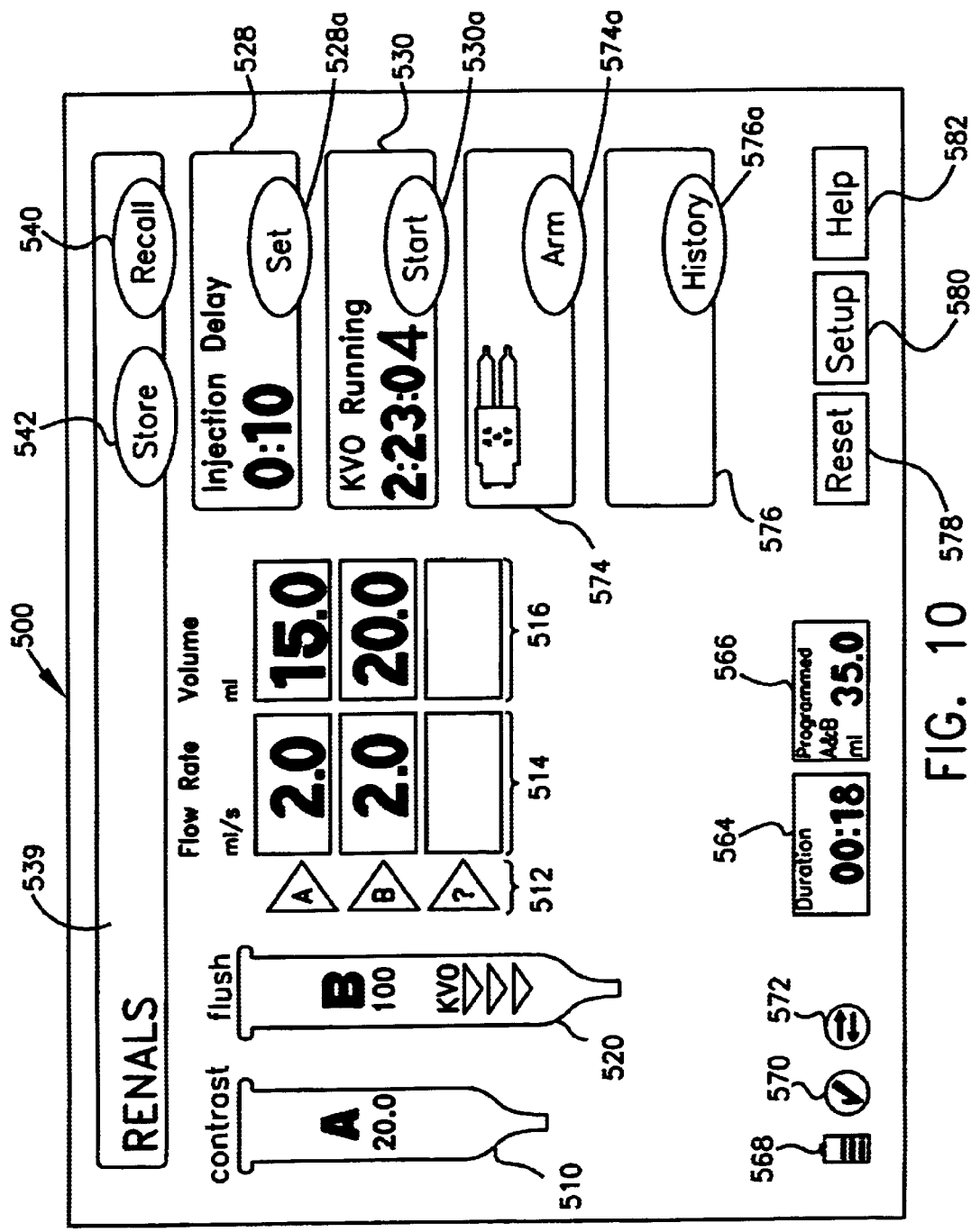
FIG. 10 is a depiction of a control screen arrangement for use with a further protocol.

FIG. 10 illustrates another protocol. Entitled "renals", the protocol set here involves an exemplary contrast phase and flush phase, as shown, for imaging the renals of a patient. Injection has not yet taken place.

As shown in FIG. 10, other touch fields and display fields may be provided within touch screen arrangement 500. For instance, an "injection delay" can be entered into a display field 528 by means of a touch field 528a suited for that purpose. The "injection delay" corresponds to a period of time that elapses between the start of imaging and the start of injection, or, between pushing "start" and the initial "surge" of fluid in an injection procedure.

A KVO display field 530 may show the status of "KVO", particularly, a countdown of the time that remains in such a state. As discussed previously, the duration of "KVO" could preferably be capped. Again, the rate, volume and frequency of delivery in "KVO" are fixed ahead of time but it could also be variably programmed by the operator, by any suitable means.

The "arm injector" display field 574 and associated touch field 574a could serve the purpose of arming the injector in a manner to be described further below.

The "history" display field 576 with associated touch field 576a may serve the purpose of recalling past injection information that has been stored.

The "protocol" display field 539 and associated touch fields 540, 542 may serve the purposes of the identification, storage and recall of user-defined (saved) injection programs or (factory) pre-loaded programs.

A "reset" touch field 578 could serve to return the touch screen 500 to an initial state, i.e., erase the parameters already entered and permit the operator to begin anew with entering a new protocol.

A "setup" touch field 580 enables the user to access the setup screen, thus allowing the user to configure various details of the injection, i.e., language, programmable KVO and other configuration-type setup features.

A "help" touch field 582 could function similarly to the "help" touch field 238 discussed previously.

FIGS. 11–20 illustrate different aspects of another protocol. In this instance, the protocol has been given a name ("Dr. Smith's Study"), as shown in field 539. It should thus be appreciated that specific protocols may be selectively stored and recalled, in order to ensure that an operator does not need to constantly re-enter parameters for the same protocol if a protocol is to be repeated on several different occasions. It will be appreciated herebelow that, in this connection, the touch screen arrangement will preferably be configured to produce, on certain occasions and in certain forms, a facsimile of the "screenshot" of the touch screen arrangement 500, or at least a portion of such a screenshot, corresponding to the full set of phases for a given protocol to thus allow a user to quickly and easily identify with one protocol or another by recognizing its general outward appearance, or "pattern".

Figure 11:
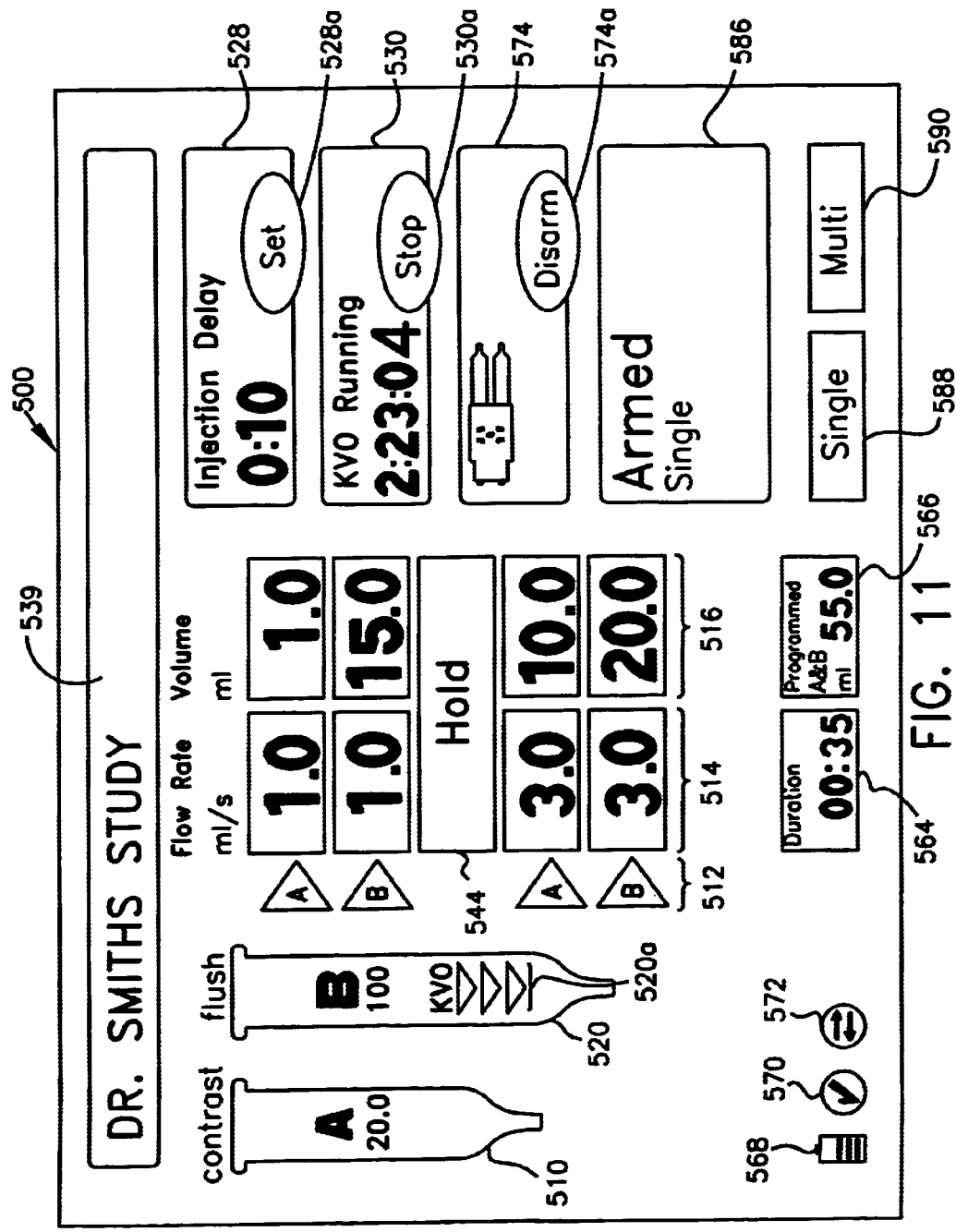
FIGS. 11–20 are depictions of control screen arrangements for use with yet another protocol.
Figure 12:
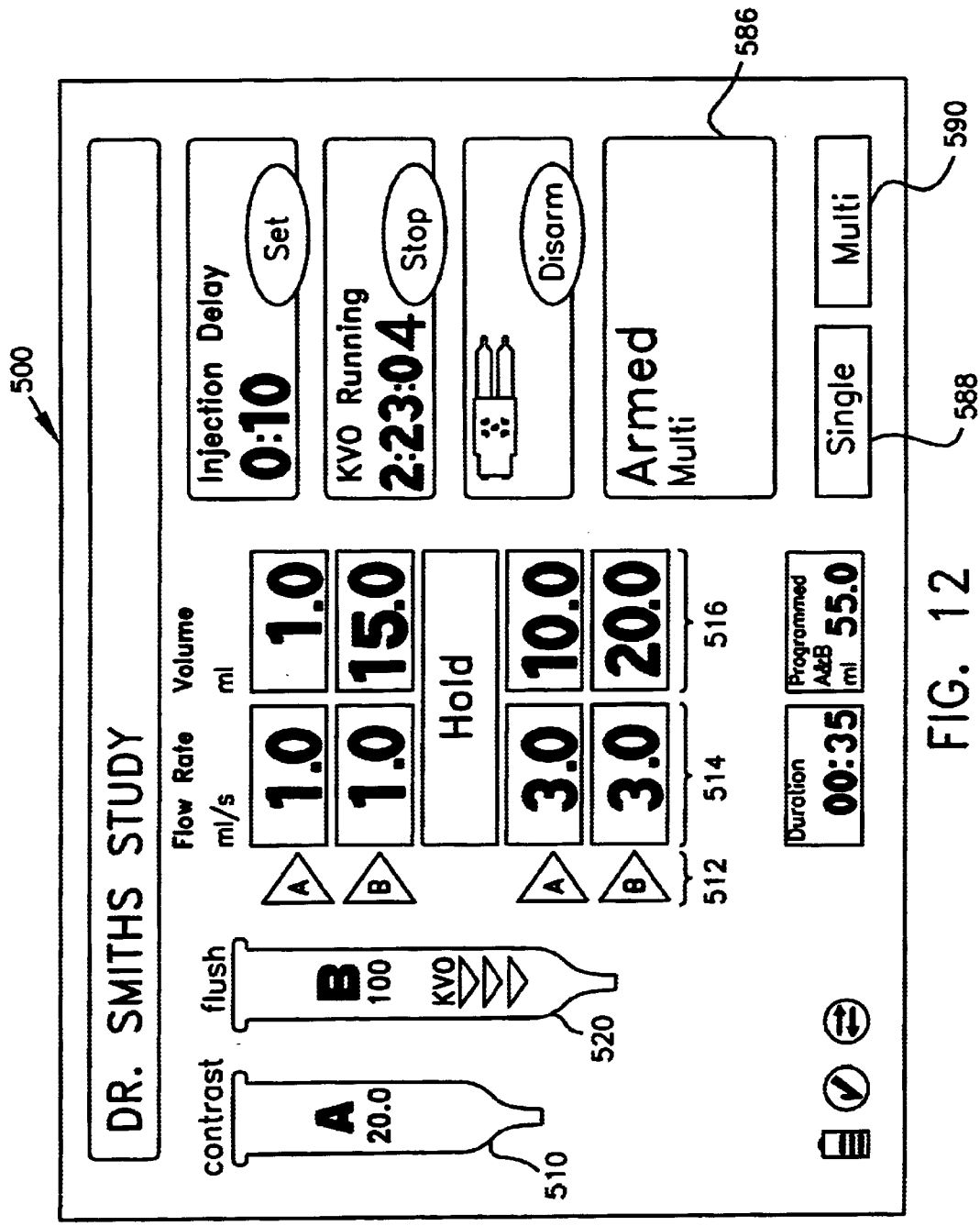

As shown in FIG. 11, a five-phase protocol has been called up, involving a contrast phase (1.0 ml at 1.0 ml/s), a flush phase (15.0 ml at 1.0 ml/s), a hold phase, a second contrast phase (10.0 ml at 3.0 ml/s) and a second flush phase (20.0 ml at 3.0 ml/s).

Preferably, "arming" the injection apparatus can be accomplished with the "arm injector" fields 574/574a discussed previously. Whereas touch field 574a may initially state "Arm" (see FIG. 10), touching that touch field will preferably prompt the appearance of display field 586 and touch fields 588, 590, as shown. Touch fields 588, 590, respectively, permit the operator to indicate whether a single injection or multiple injections, which is a repeat injection of the same protocol, are to be used.

Display field 586 will preferably indicate which of the two aforementioned options (i.e., "single" or "multi") is in effect. Whereas FIG. 11 shows that "single" has been chosen, FIG. 12 (otherwise essentially the same view as FIG. 11) shows that "multi" has been chosen.

Figure 13:
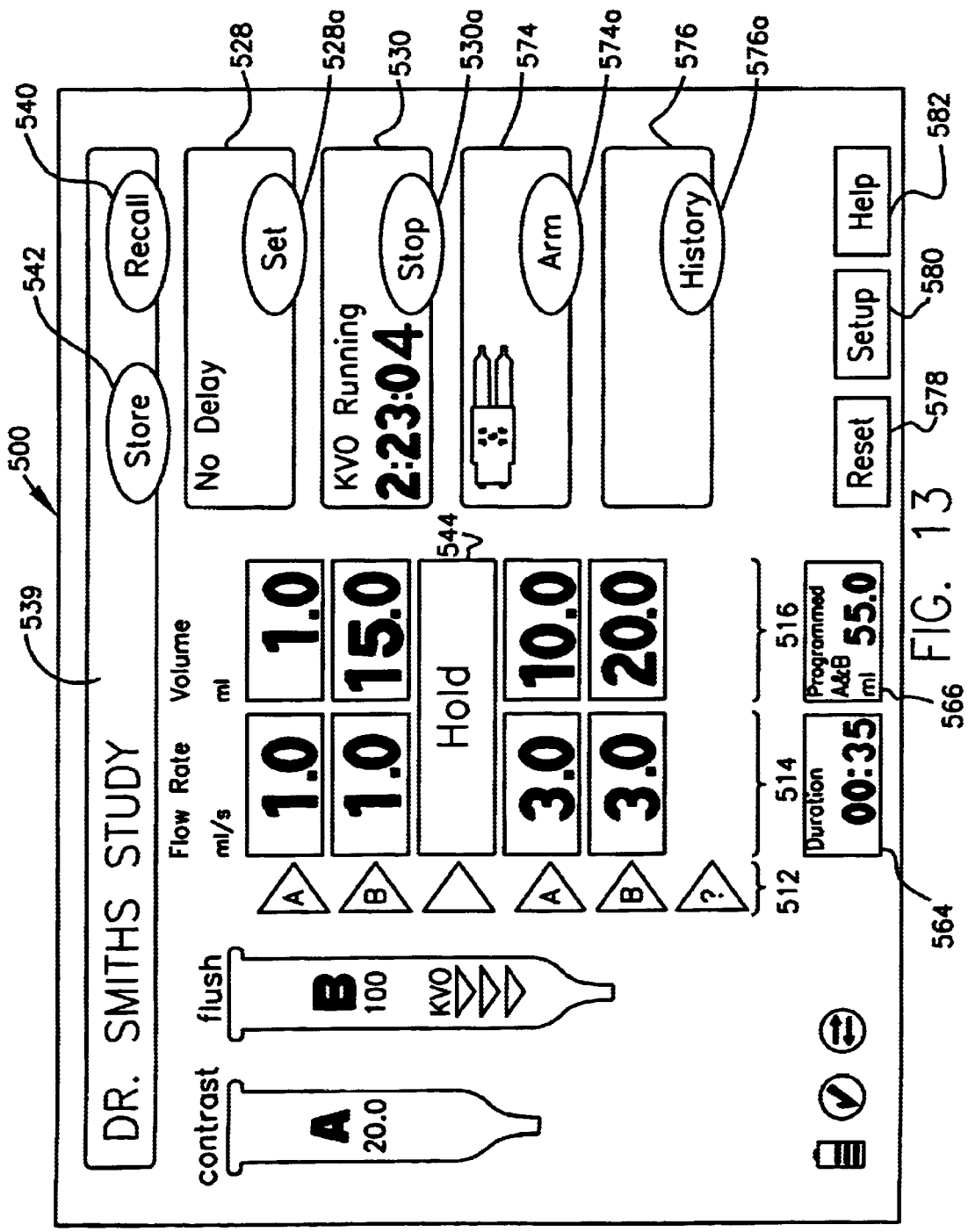

FIG. 13 illustrates the appearance of a "query" button in column 512, thus permitting the operator to subsequently enter a new phase.

Figure 14:
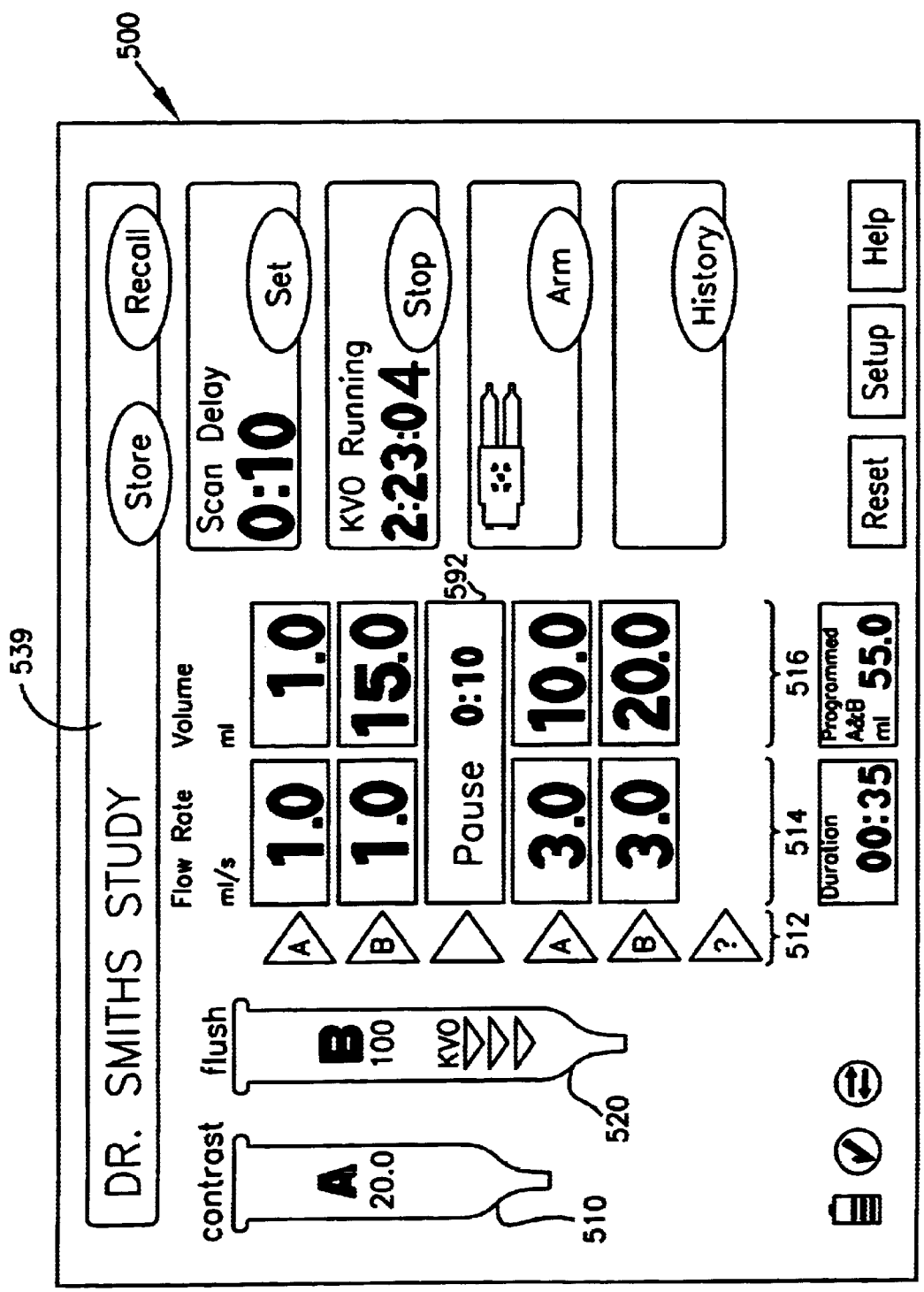

FIG. 14 is essentially the same view as FIG. 13, but shows that a "pause" phase 592 has replaced the "hold" phase. As discussed previously, a "pause" phase could represent a discrete, finite period of interruption that is predetermined.

Figure 15:
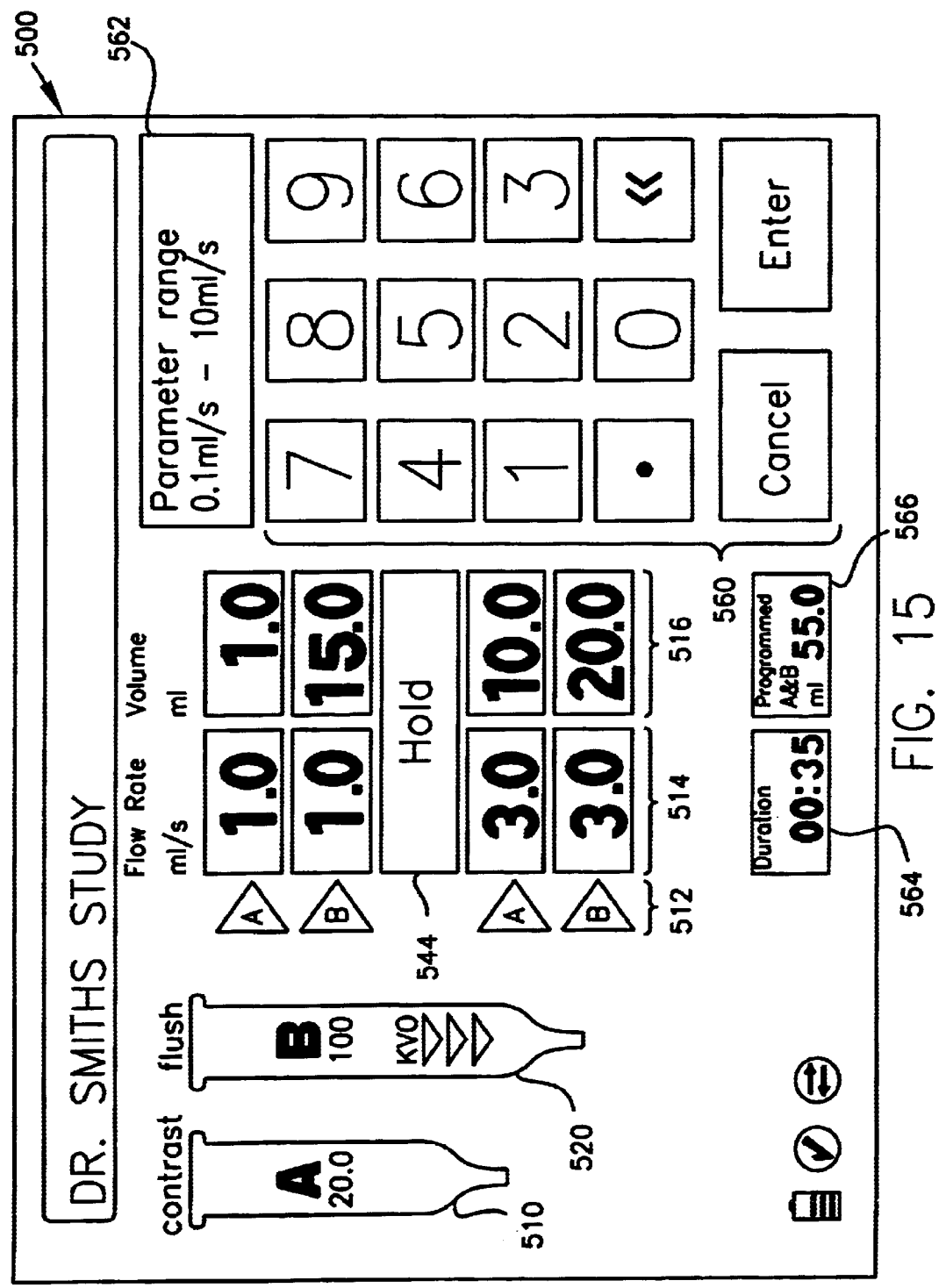

FIG. 15 is essentially the same view as FIG. 13, but shows a mode similar to that illustrated by FIG. 8, that is, an "entry" mode in which a given "protocol" field (in this case, the uppermost "flow rate" field in column 514) is highlighted as being "ready" for the entry of a new value. Thus, there is also a display field 562 here indicating parameter limits.

Figure 16:
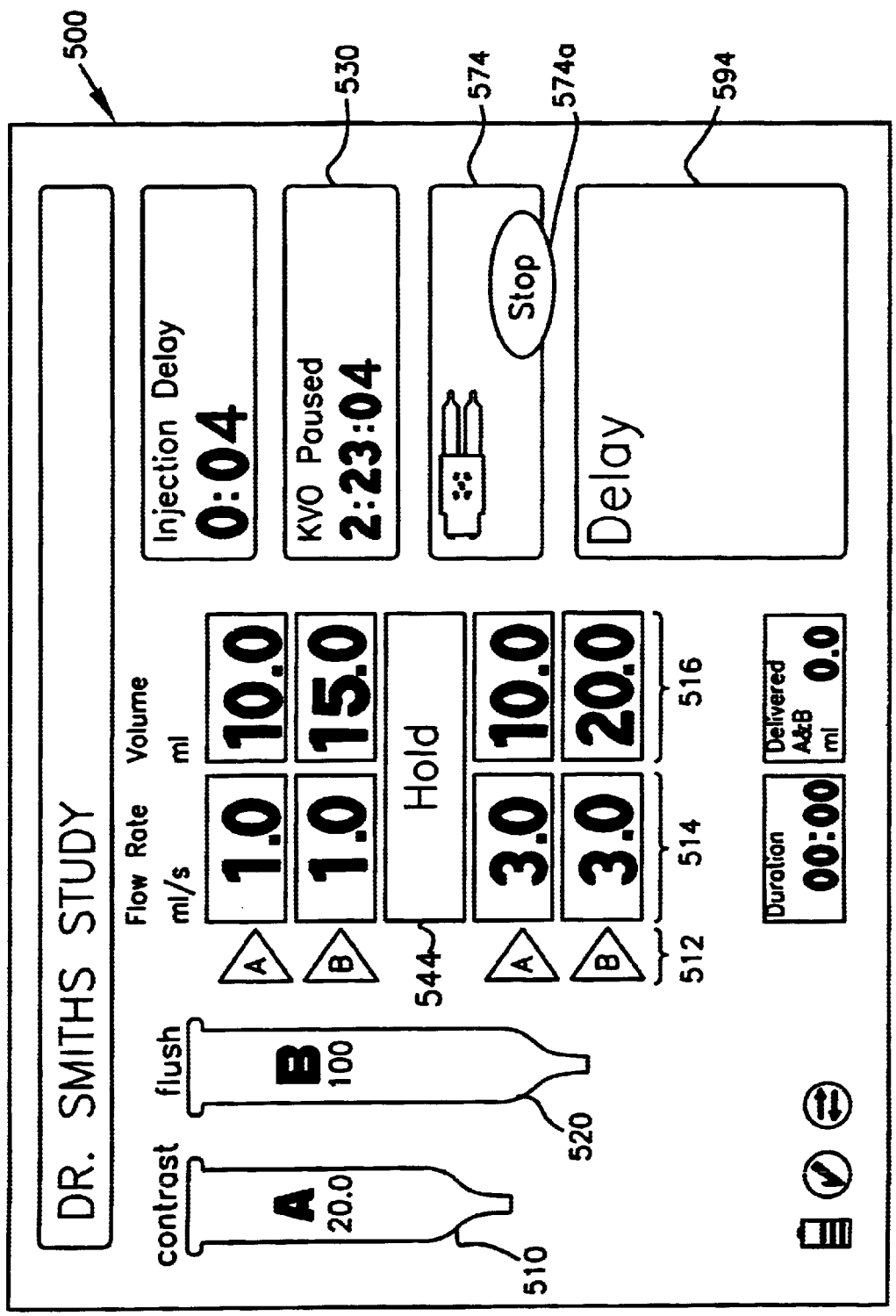

FIG. 16 is essentially the same view as FIG. 13 but conveys a state in which KVO is paused and an injection delay is taking place, prior to the start of the five protocol phases. To indicate this effect, the "protocol" fields in columns 514 and 516, including "hold" field 544, may be highlighted, perhaps with muted colors, and a display field 594 may appear to indicate that an injection delay is indeed taking place. Because the entire injection apparatus is now in an "active" mode, field 574a may now display a suitably highlighted "stop button" (perhaps in red with white lettering) that would permit the operator to abort the procedure before the first contrast phase begins. On the other hand, the operator may be apprised of the actual stage of the procedure being undertaking by suitably highlighting the "injection delay" field 528 as shown and indicating the time left in the injection delay. Whereas the "protocol" fields in columns 514 and 516, as well as hold field 544, may be in somewhat muted colors, the "injection delay" field 528 may now be somewhat more bold in appearance, perhaps with a dark border as shown and with dark lettering on a bright background in the field itself.

Figure 17:
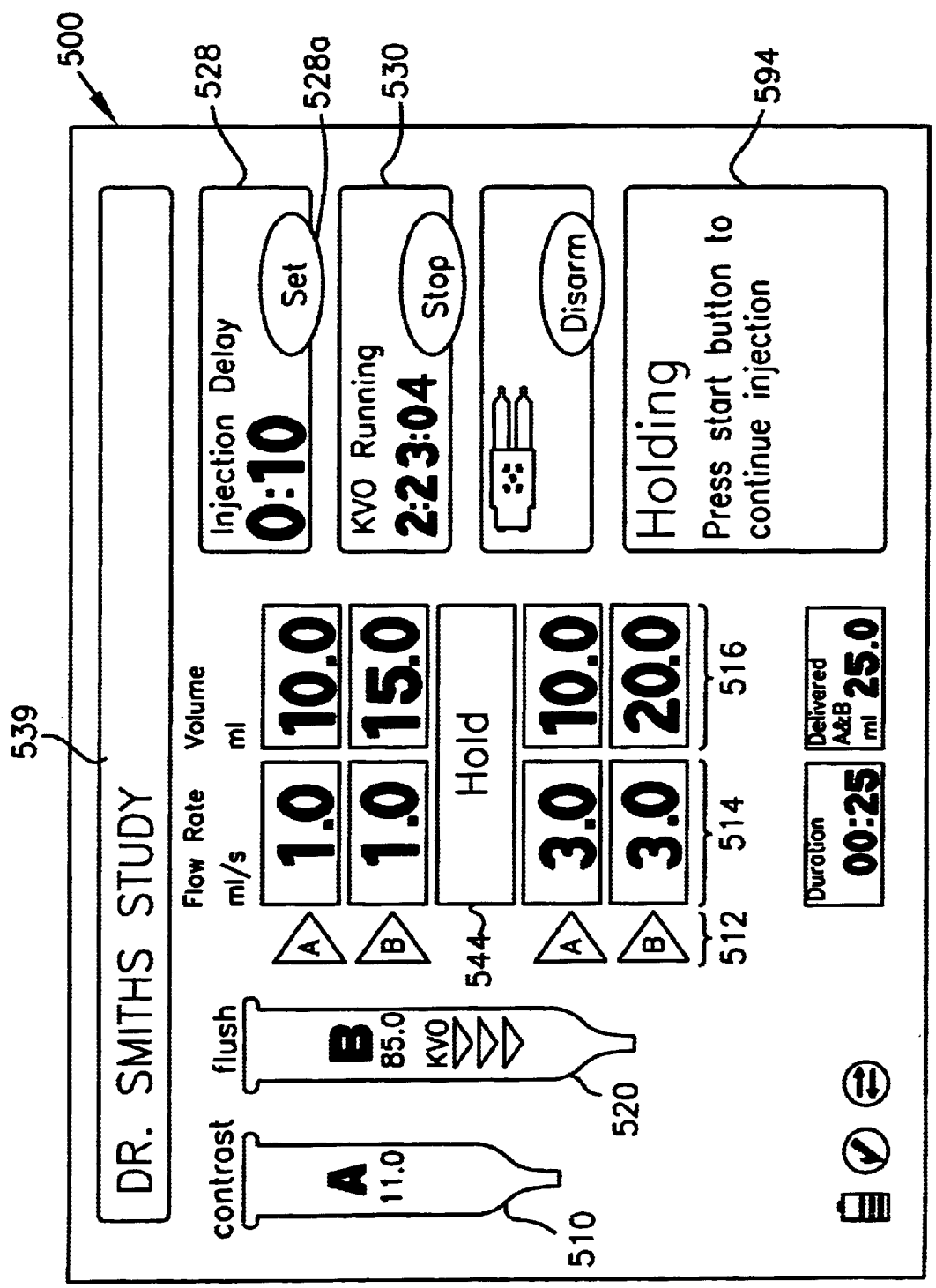
Figure 18:
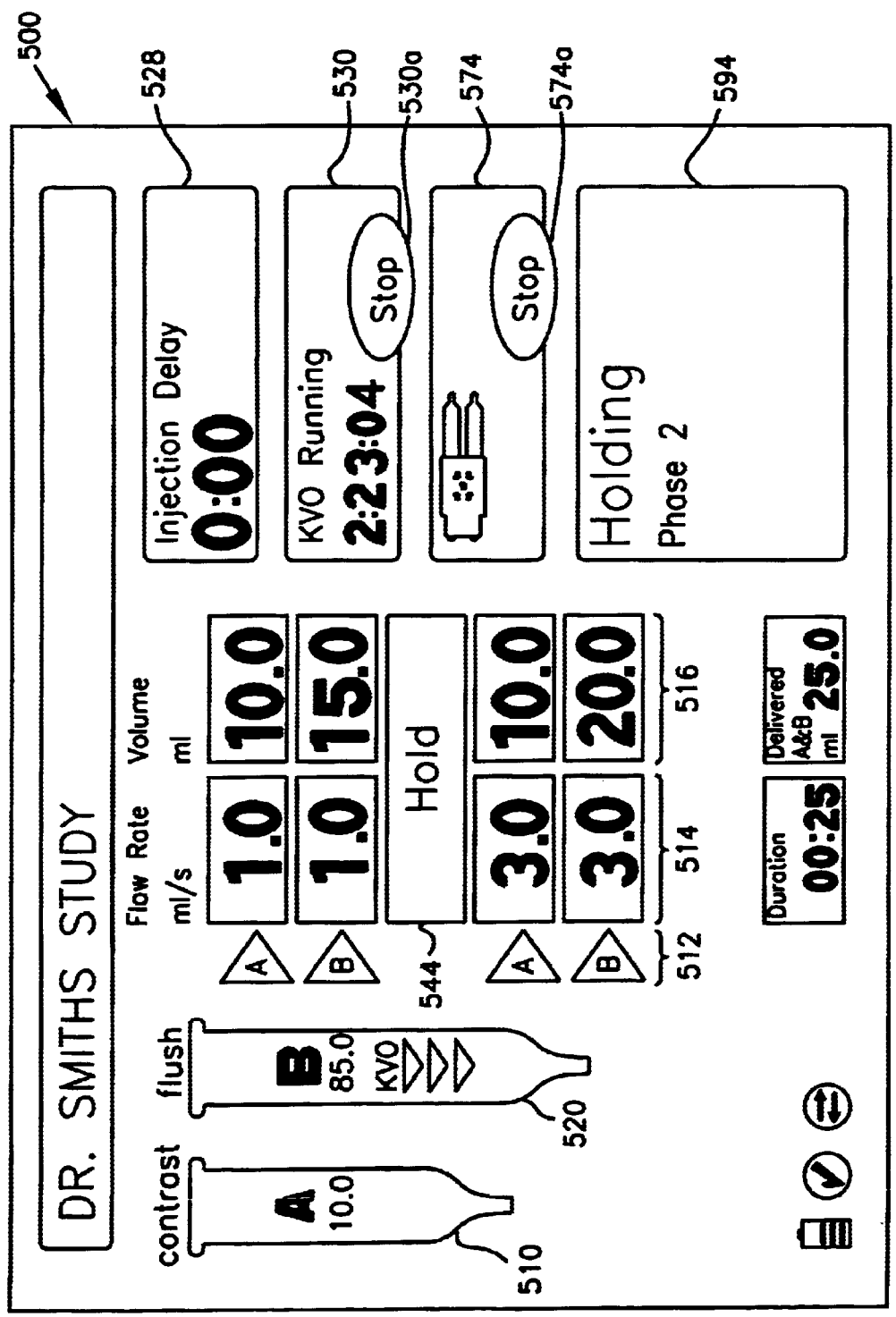
Figure 19:
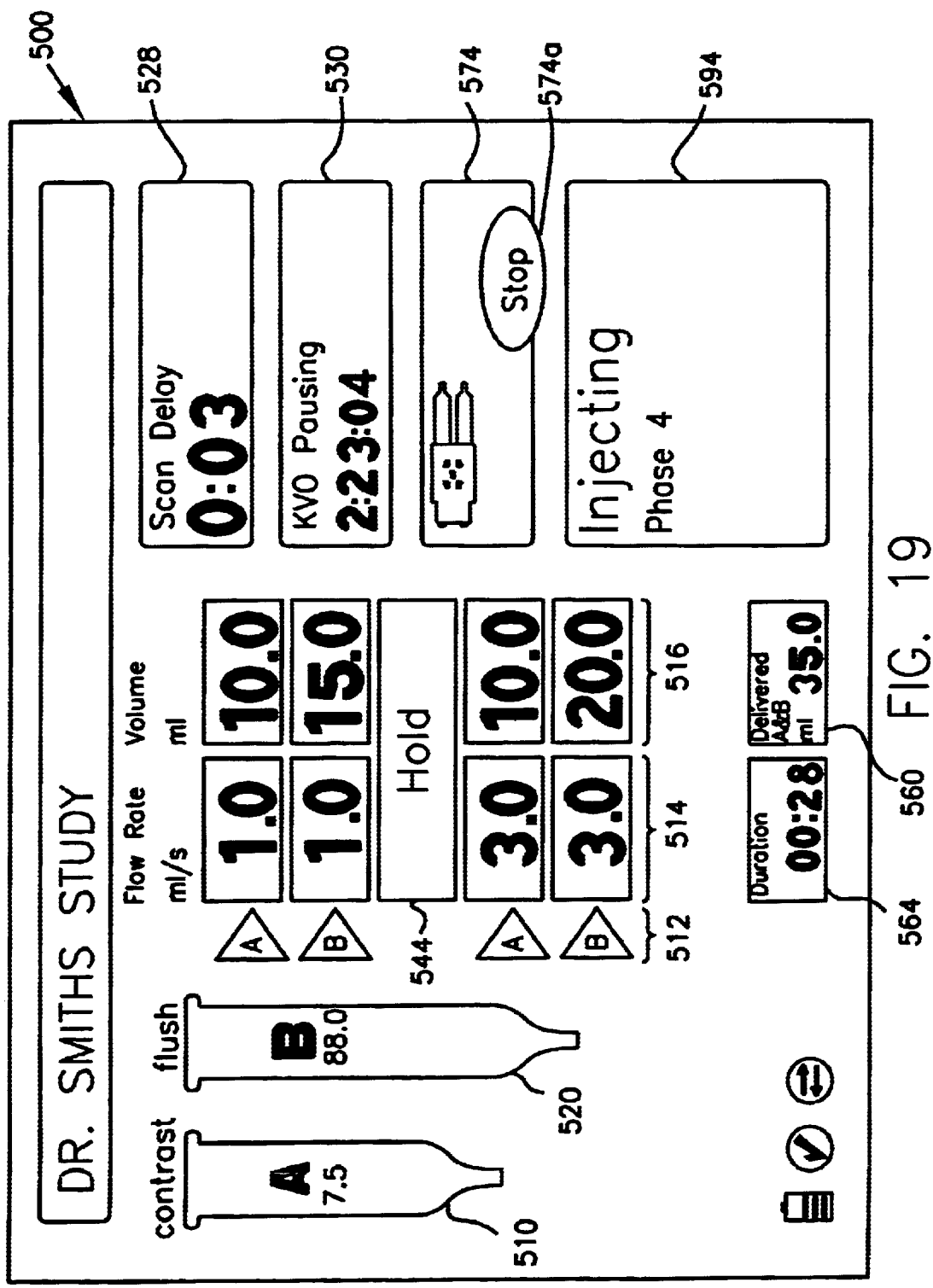

FIGS. 17, 18 and 19 illustrate the possible status of touch screen 500 at various stages of the injection protocol being employed. Preferably, a similar highlighting principle is utilized for such stages as for the "injection delay" stage as just described, that is, a field or fields relating to the actual stage or phase being undertaken is/are preferably highlighted in a manner that clearly indicates to the operator what is taking place.

Thus, FIG. 17 illustrates the possible status of touch screen 500 during the hold phase. In this case, the "hold" field 544 is highlighted with a dark border and dark lettering on a bright background. The phases already undertaken, on the other hand, are depicted in muted tones, while those that have not yet been undertaken preferably bear the "base" tones such as those depicted in FIG. 13. Display field 594 preferably indicates that the hold phase is in effect. Also, as shown, the syringe-shaped display fields 510, 520 preferably indicate visually the depletion of their respective reservoirs, both numerically and (via changing the relative shading within each field) graphically.

FIG. 18 illustrates that the second phase (in this case, a flushing phase) is in effect, via highlighting the appropriate fields in columns 512, 514 and 516, as well as the syringe-shaped display field 520. Also indicated, via field 594, is the fact that a temporary hold has been imposed within the actual phase itself. An operator may choose to do this, for instance, if a patient is experiencing discomfort and, e.g., needs to reposition the tubes, etc., that are delivering the flushing medium.

FIG. 19 illustrates that the third phase (in this case, a contrast phase) is about to be in effect and that a scan delay (defined previously) is in effect. Thus, field 528 indicates a scan delay via the type of highlighting described previously.

Figure 20:
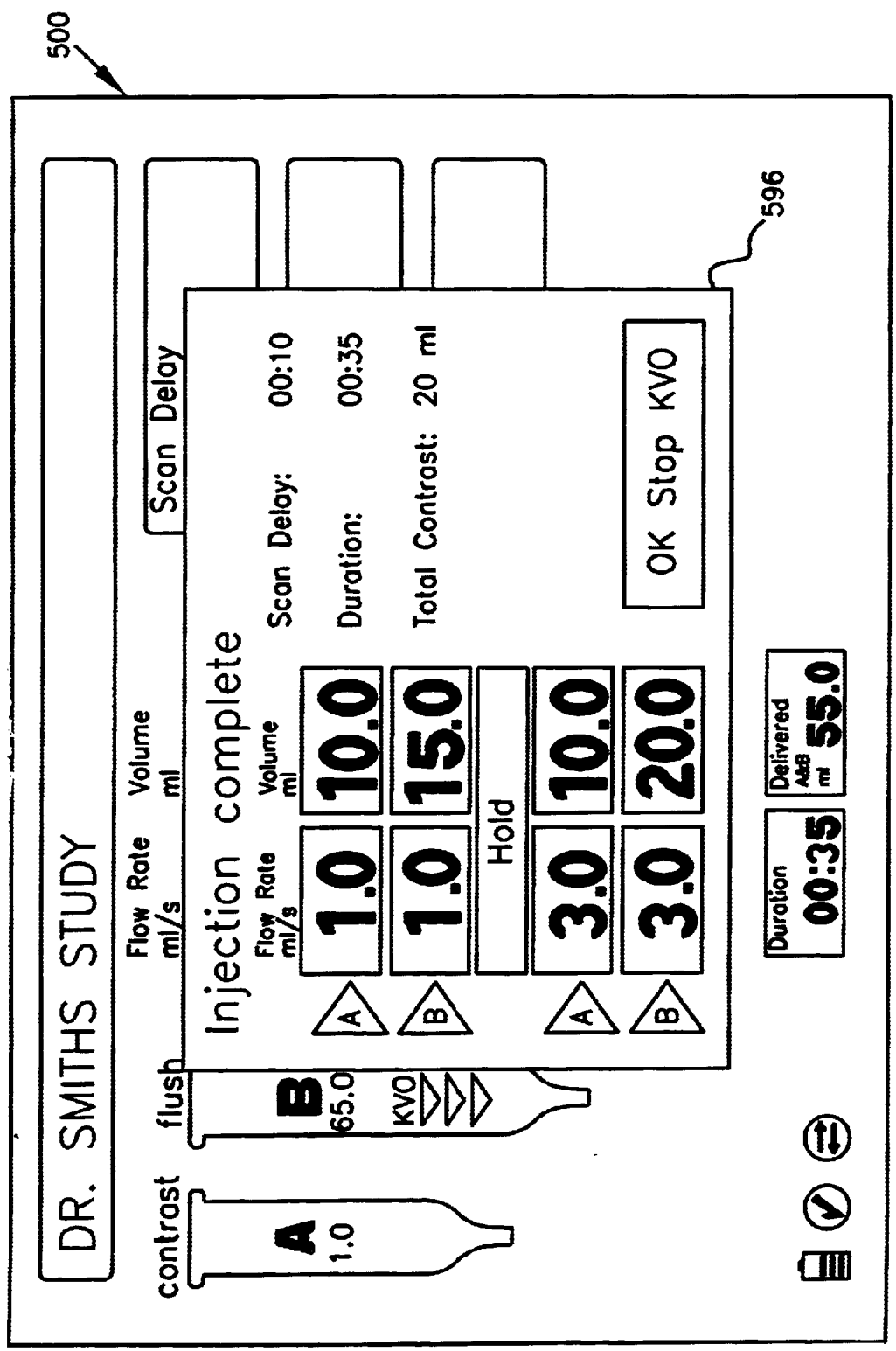

FIG. 20 illustrates what may occur once the entire protocol is completed. Preferably, a summary pop-up screen 596 may appear that provides various types of information on the phases of the protocol and of various parameters relating to it. A further touch field may be provided within the pop-up screen to permit the operator to complete the entire process by stopping "KVO".

Figure 21:
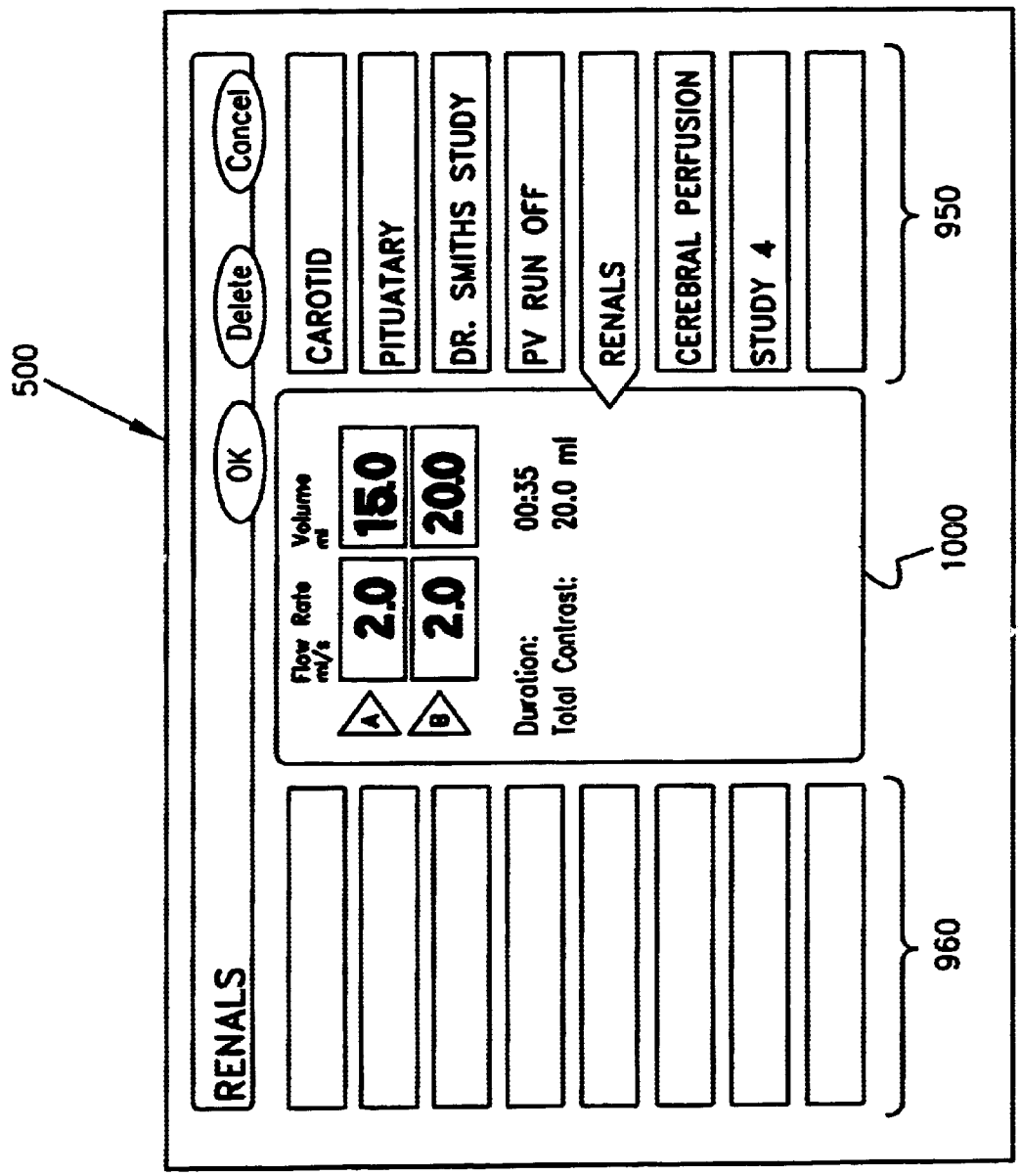
FIG. 21 is a depiction of a control screen arrangement permitting the recall of any of a number of different protocols.

FIG. 21 illustrates a "recall" feature in accordance with an embodiment of the present invention. As shown, touch screen arrangement 500 may be adapted to display a series of touch fields 950 that variously correspond to different stored protocols. As shown, additional space may be provided, such as in a column 960, to accommodate additional touch fields similar to the touch fields 950.

Preferably, by touching one of the touch fields 950, the appearance of a display field 1000 will be prompted, and this display field preferably provides, for the operator's quick and easy reference, a facsimile of the "screenshot" of touch screen arrangement 500 that would otherwise show the operator all phases of the corresponding protocol. Thus, as shown, display field 1000 (or "recall field") 1000 contains a representation of the two phases used in the "renals" protocol discussed and illustrated heretofore, though in this case the representation of the phases does not include manipulable touch fields as would otherwise be the case in a "live" screen corresponding to the "renals" protocol (such as shown in FIG. 10).

However, it will be understood that the capability is provided of being able to visually verify whether a protocol selected by one of the buttons 950 is indeed the protocol desired. At that point, if the operator wishes to execute the protocol, or at least enter a "live" screen corresponding to it for the purpose of editing it, he or she may then press the "OK" touch field (or the like) in order to switch to a "live" touch screen. Alternatively, the "recall field" capability could be exploited if the operator simply wishes to briefly review the makeup of various protocols.

It will thus be appreciated that, in connection with the "recall field" capability contemplated in connection with FIG. 21, the capability is afforded of permitting an operator to quickly and efficiently recognize the makeup of a given protocol through "pattern recognition", or through recognizing a graphical or iconic pattern of words, numbers, geometric shapes, and possibly other visual stimuli, that in sum correspond to a given protocol. (Of course, it is understood that two different stored protocols may in fact have the exact same makeup of phases and parameters.) A similar capability of "pattern recognition" was addressed heretofore, for example, in connection with the summary pop-up screen 596 shown in FIG. 20, in which the operator is able to be reminded of the makeup of a protocol immediately after it has been run.

In the context of the present disclosure, the terms "infusion" and "injection", and their grammatical derivations, are to be construed as being interchangeable and are meant to refer to essentially any of a wide range of arrangements for introducing fluid into a patient.

If not otherwise stated herein, it may be assumed that all components and/or processes described heretofore may, if appropriate, be considered to be interchangeable with similar components and/or processes disclosed elsewhere in the specification, unless an express indication is made to the contrary.

If not otherwise stated herein, any and all patents, patent publications, articles and other printed publications discussed or mentioned herein are hereby incorporated by reference as if set forth in their entirety herein.

It should be appreciated that the apparatus and method of the present invention may be configured and conducted as appropriate for any context at hand. The embodiments described above are to be considered in all respects only as illustrative and not restrictive. The scope of the invention is defined by the following claims rather than the foregoing description. All changes that come within the meaning and range of equivalency of the claims are to be embraced within their scope.

What is claimed is:
1. A fluid injection apparatus comprising:
   at least one drive mechanism;
   at least two fluid containers operably associated with the at least one drive mechanism, one fluid container containing a contrast medium and the other fluid container containing a flushing medium; and
   a control device operably associated with the at least one drive mechanism;

wherein said control device is adapted to allow an operator to:
selectively program a plurality of phases of an injection procedure, a first phase comprising a flushing medium phase and a second phase comprising a contrast medium phase; and
selectively modify at least one phase of the injection procedure.

2. The apparatus according to claim 1, wherein said control device is operable to abort an injection procedure while the injection procedure is taking place.

3. The apparatus of claim 1, wherein at least one of the two fluid containers comprises a syringe.

4. The apparatus according to claim 1, wherein each of the plurality of phases is defined by at least two injection parameters selected from fluid flow rate, fluid volume and injection duration.

5. The apparatus according to claim 1, wherein said control device is further adapted to allow the operator to program a KVO phase.

6. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism;
wherein at least one of said fluid containers includes an illumination element; and
wherein said control device includes at least one element affiliated with said illumination element.

7. The apparatus according to claim 6, wherein said illumination element is adapted to produce colored light.

8. The apparatus according to claim 6, wherein:
said illumination element is associated with a color; and
said at least one element of said control device comprises an element associated with the color of said illumination element.

9. The apparatus according to claim 8, wherein said at least one element of said control device includes a computer screen icon.

10. The apparatus according to claim 6, wherein:
each of said fluid containers comprises an illumination element;
said at least one element of said control device comprising at least two elements, each of which is affiliated with a corresponding one of said illumination elements.

11. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism;
wherein the control device is adapted to be used by an operator to:
(i) selectively program a plurality of phases of an injection procedure, at least one of the phases comprising a contrast medium phase, a flushing medium phase, a pause phase or a hold phase;
(ii) produce, during programming, a graphical display indicating the programmed phases, the graphical display including a screen display field corresponding to the phases or a distinct color scheme associated with the phases; and
(iii) selectively recreate a facsimile of the graphical display at a subsequent time.

12. The apparatus according to claim 11, wherein said control device is operable to recreate a facsimile of said graphical display at least at one of the following times: prior to an injection procedure, during an injection procedure and immediately subsequent to an injection procedure.

13. The apparatus according to claim 11, wherein said control device is operable to:
store a protocol comprising a plurality of phases;
store a graphical display corresponding to said protocol; and
recall the stored protocol, wherein a facsimile of the graphical display corresponding to the stored protocol is recreated.

14. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism;
wherein said control device is operable to selectively program a plurality of phases of an injection procedure, at least one phase comprising one of: a contrast medium phase and a flushing medium phase;
wherein said control device is further operable to selectively establish and control a KVO state independently from the programming of any of said phases.

15. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism;
wherein said control device is adapted to allow an operator to selectively program a plurality of phases of an injection procedure;
at least one phase comprising a contrast medium phase or a flushing medium phase; and
at least another phase comprising a hold phase, the hold phase operable to allow the operator to modify one or more injection parameters of a subsequent phase.

16. The apparatus according to claim 15, wherein said control device further comprises a delay time clock, said control device further being operable to program the delay time clock during said hold phase.

17. The apparatus according to claim 15, wherein the hold phase is of indefinite duration.

18. The apparatus according to claim 15, wherein KVO occurs during the hold phase.

19. A fluid injection apparatus comprising:
at least one drive mechanism;
at least two fluid containers operably associated with the at least one drive mechanism, one fluid container containing a contrast medium and the other fluid container containing a flushing medium; and
a control device operably associated with the at least one drive mechanism;

wherein said control device is adapted to allow an operator to selectively program a plurality of phases of an injection procedure, a first phase comprising a flushing medium phase and a second phase comprising a contrast medium phase;

said control device further being adapted to allow the operator to selectively store a protocol comprising the programmed phases and selectively recall said protocol at a subsequent time for use in an injection procedure.

20. A fluid injection apparatus comprising:

at least one drive mechanism;

at least two fluid containers operably associated with the at least one drive mechanism, one fluid container containing a contrast medium and the other fluid container containing a flushing medium; and a control device operably associated with the at least one drive mechanism;

wherein said control device is adapted to allow an operator to selectively program a plurality of phases of an injection procedure;

a first phase comprising a contrast medium phase or a flushing medium phase;

a second phase comprising a contrast medium phase or a flushing medium phase; and at least another phase comprising a pause phase programmed to occur between the first and second phases, the pause phase adapted to be programmable for a fixed duration of time.

21. The apparatus according to claim 20 wherein the second phase automatically commences after the end of the pause phase.

22. A method of operating an injector providing visual stimuli corresponding to an injection protocol, the method comprising:

perceiving the visual stimuli;

recognizing a pattern provided by the stimuli;

correlating the recognized pattern to the injection protocol; and interacting with the injector based on the recognized pattern.

23. The method according to claim 22 wherein the visual stimuli is graphical or iconic.

24. The method according to claim 23 wherein the visual stimuli comprises one or more of words, numbers, shapes and colors.

25. The method according to claim 22 wherein the step of interacting comprises programming the injector.

26. A fluid injection apparatus comprising:

at least one drive mechanism;

at least two fluid containers operably associated with the at least one drive mechanism, one fluid container containing a contrast medium and the other fluid container containing a flushing medium; and a control device operably associated with the at least one drive mechanism, the control device adapted to allow an operator to:

(i) program a plurality of phases of an injection procedure, at least one of the phases comprising a contrast medium phase, a flushing medium phase, a pause phase or a hold phase;

(ii) modify at least one phase of the injection procedure; and (iii) abort an injection procedure while the injection procedure is taking place.

27. The apparatus of claim 26 wherein at least one of the two fluid containers comprises a syringe.

28. The apparatus of claim 26 wherein a first phase comprises a flushing medium phase and a second phase comprises a contrast medium phase.

29. The apparatus of claim 26 wherein each of the plurality of phases is defined by at least two injection parameters selected from fluid flow rate, fluid volume and injection duration.

30. The apparatus of claim 26 wherein the control device is further adapted to allow the operator to program a KVO phase.

31. The apparatus of claim 26 wherein the control device comprises a touch screen.

32. The apparatus of claim 26 wherein the at least one drive mechanism comprises two drive mechanisms and each of the fluid containers is adapted to be operably connected to a respective one of the two drive mechanisms.

33. The apparatus of claim 1 wherein the control device is further adapted to allow the operator to program a KVO phase.

34. The apparatus of claim 1 wherein the control device comprises a touch screen.

35. The apparatus of claim 1 wherein the at least one drive mechanism comprises two drive mechanisms and each of the fluid containers is adapted to be operably connected to a respective one of the two drive mechanisms.

36. The apparatus of claim 1 wherein the control device is further adapted to allow the operator to program a pause phase.

37. The apparatus of claim 36 wherein the pause phase is programmed for a fixed duration of time.

38. The apparatus of claim 1 wherein the control device is further adapted to allow the operator to program a hold phase.

39. The apparatus of claim 6 wherein at least one of the two fluid containers comprises a syringe.

40. The apparatus of claim 6 wherein the control device comprises a touch screen.

41. The apparatus of claim 6 wherein the at least one drive mechanism comprises two drive mechanisms and each of the fluid containers is adapted to be operably connected to a respective one of the two drive mechanisms.

42. The apparatus of claim 11 wherein the control device comprises a touch screen.

43. The apparatus of claim 14 wherein at least one of the two fluid containers comprises a syringe.

44. The apparatus of claim 14 wherein the control device comprises a touch screen.

45. The apparatus of claim 14 wherein the at least one drive mechanism comprises two drive mechanisms and each of the fluid containers is adapted to be operably connected to a respective one of the two drive mechanisms.

46. The apparatus of claim 14 wherein each of the at least two fluid containers comprises a syringe.

47. The apparatus of claim 14 wherein the KVO state is defined by at least fluid flow rate.

48. A fluid injection apparatus comprising:

at least one drive mechanism;

at least two fluid containers operably associated with the at least one drive mechanism, one fluid container containing a contrast medium and the other fluid container containing a flushing medium; and a control device operably associated with the at least one drive mechanism;

wherein said control device is adapted to allow an operator to selectively program a plurality of phases of an injection procedure, at least one phase comprising a contrast medium phase or a flushing medium phase, and at least another phase comprising a hold phase, wherein KVO occurs during the hold phase.

49. The apparatus of claim 48 wherein the hold phase allows an operator to modify one or more injection parameters of a subsequent phase.

50. The apparatus of claim 48 wherein the control device comprises a delay time clock that is adapted to allow the operator to program the delay time clock during the hold phase.

51. The apparatus of claim 48 wherein the hold phase is of indefinite duration.

52. The apparatus of claim 48 wherein at least one of the two fluid containers comprises a syringe.

53. The apparatus of claim 48 wherein each of the plurality of phases is defined by at least two injection parameters selected from fluid flow rate, fluid volume and injection duration.

54. The apparatus of claim 48 wherein the control device comprises a touch screen.

55. The apparatus of claim 48 wherein the at least one drive mechanism comprises two drive mechanisms and each of the fluid containers is adapted to be operably connected to a respective one of the two drive mechanisms.

56. A fluid injection apparatus comprising:

at least one drive mechanism;

at least two fluid containers operably associated with the at least one drive mechanism, one fluid container containing a contrast medium and the other fluid container containing a flushing medium; and a control device operably associated with the at least one drive mechanism;

wherein the control device is adapted to allow an operator to selectively program a plurality of phases of an injection procedure, a first phase comprising a contrast medium phase or a flushing medium phase, a second phase comprising a pause phase, and a third phase comprising a contrast medium phase or a flushing medium phase, wherein the third phase automatically commences after the end of the pause phase.

57. The apparatus of claim 56 wherein the control device is further adapted to allow programming of a hold phase, which allows an operator to modify one or more injection parameters of a subsequent phase.

58. The apparatus of claim 57 wherein the hold phase is of indefinite duration.

59. The apparatus of claim 56 wherein at least one of the two fluid containers comprises a syringe.

60. The apparatus of claim 56 wherein each of the plurality of phases is defined by at least two injection parameters selected from fluid flow rate, fluid volume and injection duration.

61. The apparatus of claim 56 wherein the control device comprises a touch screen.

62. The apparatus of claim 56 wherein the at least one drive mechanism comprises two drive mechanisms and each of the fluid containers is adapted to be operably connected to a respective one of the two drive mechanisms.

63. A fluid injection apparatus comprising:

a first drive mechanism;

a first syringe adapted to be operably engaged with the first drive mechanism, the first syringe containing a contrast medium;

a second drive mechanism;

a second syringe adapted to be operably engaged with the second drive mechanism, the second syringe containing a flushing medium; and a control device operably associated with the first and second drive mechanisms, the control device being adapted to allow an operator to (i) selectively program a plurality of phases of an injection procedure, at least one of the phases comprising a contrast medium phase or a flushing medium phase, and (ii) selectively establish a KVO phase independently from the other phases.

64. The apparatus of claim 63 wherein the control device comprises a touch screen.

65. The apparatus of claim 63 wherein the KVO phase is defined by at least fluid flow rate.

66. The apparatus of claim 63 wherein the control device is further adapted to allow the operator to abort the injection procedure.

67. The apparatus of claim 63 wherein the control device is further adapted to allow the operator to program a hold phase.

68. The apparatus of claim 63 wherein the control device is further adapted to allow the operator to program a pause phase.

69. A fluid injection apparatus comprising:

a first drive mechanism;

a first syringe adapted to be operably engaged with the first drive mechanism, the first syringe containing a contrast medium;

a second drive mechanism;

a second syringe adapted to be operably engaged with the second drive mechanism, the second syringe containing a flushing medium; and a control device operably associated with the first and second drive mechanisms, the control device being adapted to allow an operator to selectively program a plurality of phases of an injection procedure, a first phase comprising a contrast medium phase or a flushing medium phase, a second phase comprising a contrast medium phase or a flushing medium phase, and a third phase comprising a contrast medium phase or a flushing medium phase, and a KVO phase independent from the other phases.

70. The apparatus of claim 48 wherein a first phase comprises a flushing medium phase and a second phase comprises a contrast medium phase.

* * * * *